(12) United States Patent
Jang et al.

(10) Patent No.: US 12,174,174 B2
(45) Date of Patent: Dec. 24, 2024

(54) COMPOSITION COMPRISING MATERIAL FOR REGULATING OCT4 MODIFICATION TO REPRESS STEMNESS

(71) Applicant: NATIONAL CANCER CENTER, Goyang-si (KR)

(72) Inventors: Hyonchol Jang, Seoul (KR); Dong Keon Kim, Goyang-si (KR)

(73) Assignee: NATIONAL CANCER CENTER, Goyang-si (KR)

( * ) Notice: Subject to any disclaimer, the term of this patent is extended or adjusted under 35 U.S.C. 154(b) by 854 days.

(21) Appl. No.: 17/285,710

(22) PCT Filed: Dec. 6, 2018

(86) PCT No.: PCT/KR2018/015444
§ 371 (c)(1),
(2) Date: Apr. 15, 2021

(87) PCT Pub. No.: WO2020/091137
PCT Pub. Date: May 7, 2020

(65) Prior Publication Data
US 2022/0034872 A1 Feb. 3, 2022

(30) Foreign Application Priority Data

Oct. 31, 2018 (KR) .................. 10-2018-0132592
Oct. 31, 2018 (KR) .................. 10-2018-0132593
Oct. 31, 2018 (KR) .................. 10-2018-0132594

(51) Int. Cl.
*G01N 33/50* (2006.01)
*C07K 14/47* (2006.01)
*G01N 33/68* (2006.01)

(52) U.S. Cl.
CPC ..... *G01N 33/5073* (2013.01); *C07K 14/4702* (2013.01); *G01N 33/6854* (2013.01); *G01N 2440/14* (2013.01)

(58) Field of Classification Search
None
See application file for complete search history.

(56) References Cited

U.S. PATENT DOCUMENTS

| | | | | |
|---|---|---|---|---|
| 7,435,591 | B2 * | 10/2008 | Malek | C07K 14/4738 435/375 |
| 2016/0324934 | A1 * | 11/2016 | Angel | A61K 38/44 |
| 2016/0369243 | A1 * | 12/2016 | Kariko | C12N 9/22 |
| 2018/0231568 | A1 | 8/2018 | Youn et al. | |

FOREIGN PATENT DOCUMENTS

KR 10-2012-0082849 A 7/2012
KR 10-2018-0093657 A 8/2018

OTHER PUBLICATIONS

"Transgenic Mouse Methods and Protocols" p. 245-256; publication year 2011 Editor Hofker et al. (Year: 2011).*
International Search Report issued on Jul. 19, 2019 in PCT/KR2018/015444 filed on Dec. 6, 2018, 6 pages.
Bae, K. B. et al., "Serine 347 phosphorylation by JNKs Negatively Regulates OCT4 Protein Stability in Mouse Embryonic Stem Cells," Stem Cell Reports, vol. 9, 2017, pp. 2050-2064.
Spelat, R. et al., "Serine 111 Phosphorylation Regulates OCT4A Protein Subcellular Distribution and Degradation," The Journal of Biological Chemistry, vol. 287, No. 45, 2012, pp. 38279-38288.
Shin, J. et al., "Aurkb/PP1-mediated resetting of Oct4 during the cell cycle determines the identity of embryonic stem cells," eLife, vol. 5, e10877, 2016, pp. 1-21.
Campbell, P. A. et al., "Oct4 Targets Regulatory Nodes to Modulate Stem Cell Function," PLoS ONE, Issue 6, e553, 2007, pp. 1-11.
Brumbaugh, J. et al., "Phosphorylation regulates human OCT4," PNAS, vol. 109, No. 19, 2012, pp. 7162-7168.
Campbell, P. A. et al., "Oct4 Interaction with Hmgb2 Regulates Akt Signaling and Pluripotency," Stem Cells, vol. 31, 2013, 15 total pages.
Jin. W. et al., "Critical POU domain residues confer Oct4 uniqueness in somatic cell reprogramming," Scientific Reports, vol. 6, Article 20818, 2016, 41 total pages.
Choi, S. et al., "Regulation of Pluripotency-related Genes and Differentiation in Mouse Embryonic Stem Cells by Direct Delivery of Cell-penetrating Peptide-conjugated CARM1 Recombinant Protein," Development & Reproduction, vol. 17, No. 1, 2013, pp. 9-16.
Nitta, R. T. et al., "Casein kinase 2a regulates glioblastoma brain tumor-initiating cell growth through the β-catenin pathway," Oncogene, vol. 34, 2015, pp. 3688-3699.
Lee, S. H. et al., "Wnt/β-catenin signalling maintains self-renewal and tumourigenicity of head and neck squamous cell carcinoma stem-like cells by activating Oct4," Journal of Pathology, vol. 234, 2014, pp. 99-107.

* cited by examiner

*Primary Examiner* — Changhwa J Cheu
(74) *Attorney, Agent, or Firm* — Oblon, McClelland, Maier & Neustadt, L.L.P.

(57) ABSTRACT

The present invention relates to a composition for repressing the sternness of stem cells, which comprises a material for regulating OCT4 modification. The material for regulating OCT4 modification according to the present invention may regulate the phosphorylation or methylation of OCT4 and inhibit Wnt signaling, thereby effectively reducing the sternness of various stem cells. Therefore, since it can be effectively used in inhibition of proliferation, recurrence and metastasis of cancer, and inhibition of resistance to an anticancer agent, and can reduce sternness even in normal stem cells, it is expected that the time for differentiation of embryonic stem cells into specific cells is shortened, and efficiency is increased.

9 Claims, 26 Drawing Sheets
Specification includes a Sequence Listing.

FIG. 7
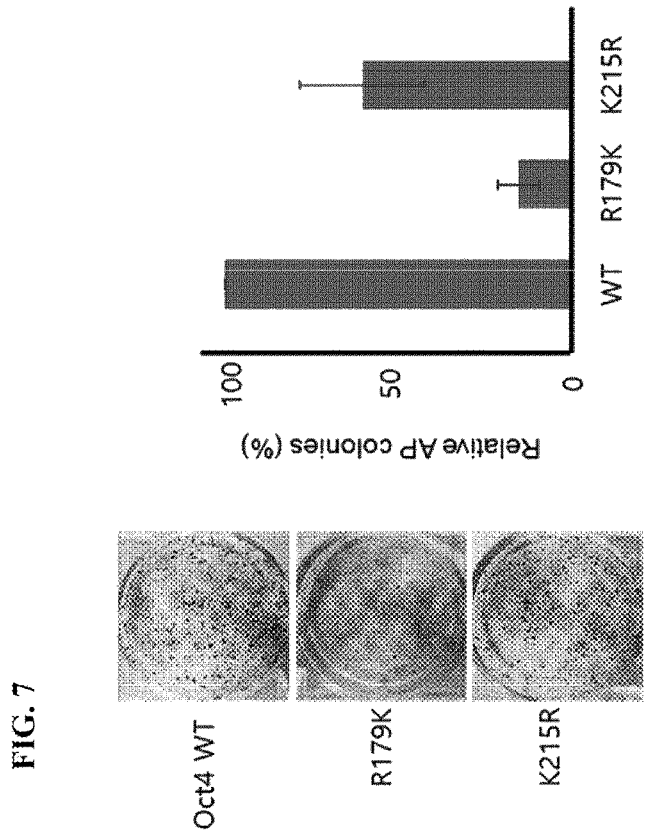
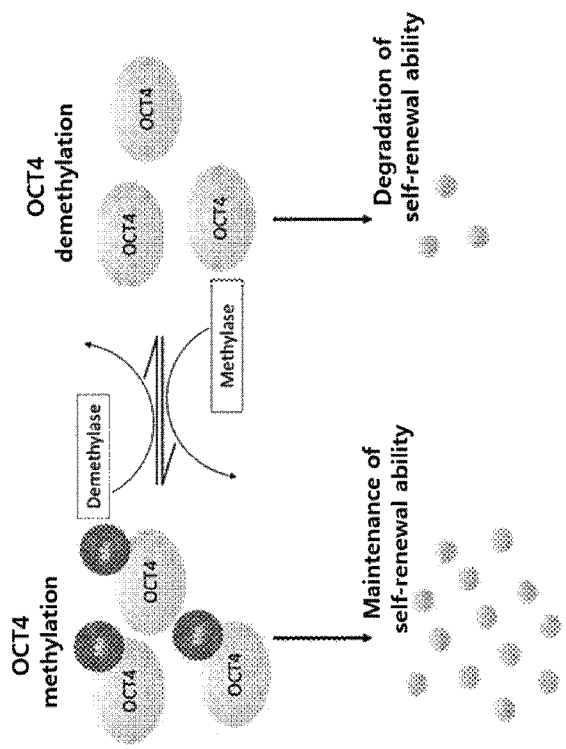

FIG. 8

Antigen Designed:

| No | start | Antigenic Determinant | Length | Antigenicity/Surface/Hydrophilicity | Disordered Score | Synthesis | Mus musculus\|Oryctolagus cuniculus blast |
|---|---|---|---|---|---|---|---|
| 1 | 26 | SVPVTALGSPMHSN | 14 | 0.27/0.79/-0.52 | 0.1296 | Easy | 100% \| 92% |
| 2 | 25 | PSVPVTALGSPMHS | 14 | 0.26/0.79/-0.50 | 0.1129 | Easy | 100% \| 92% |

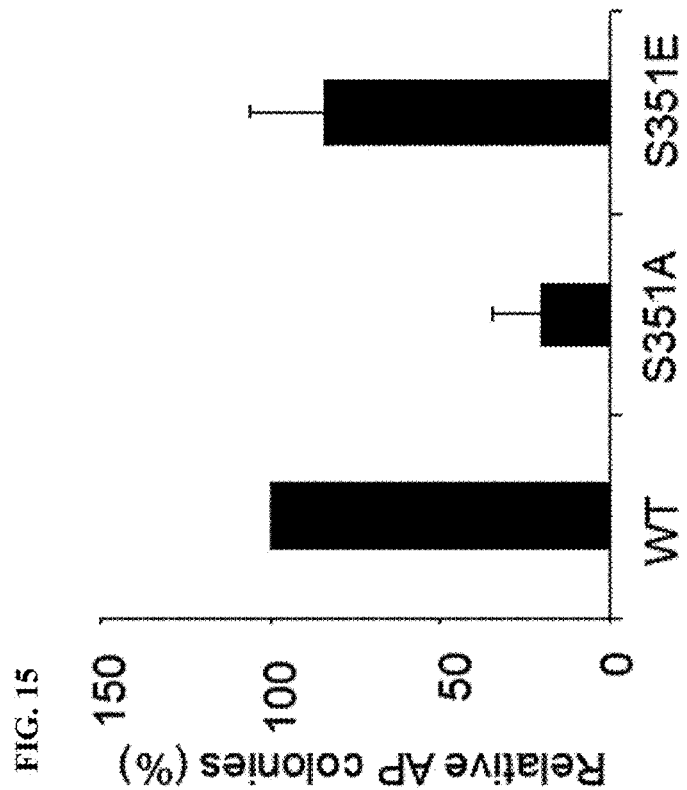
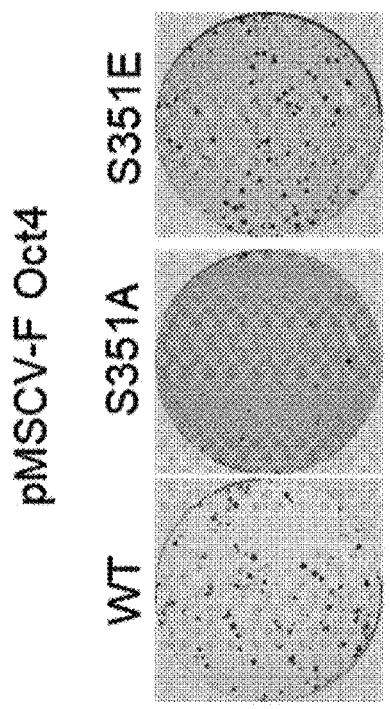
FIG. 15

[Fig. 16]
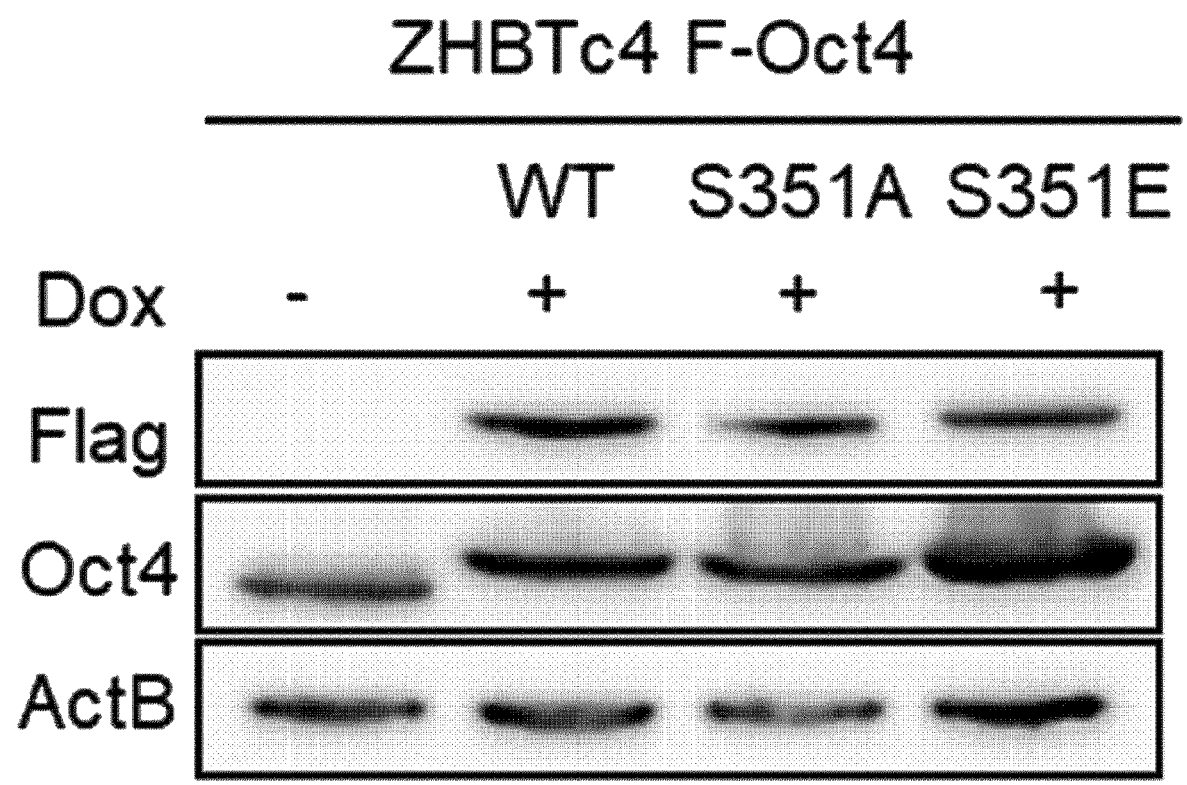

[Fig. 17]
ZHBTc4 F-Oct4
| WT | S351A | S351E |
|---|---|---|
| 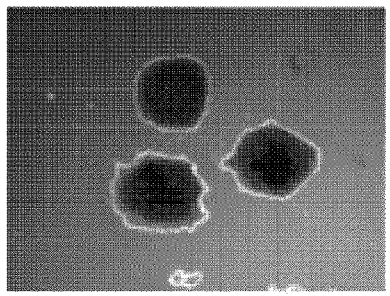 | 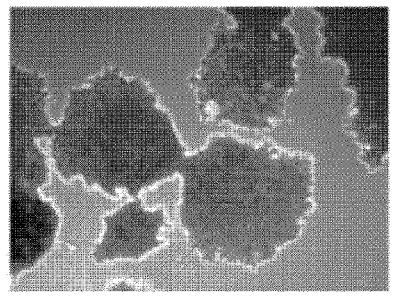 | 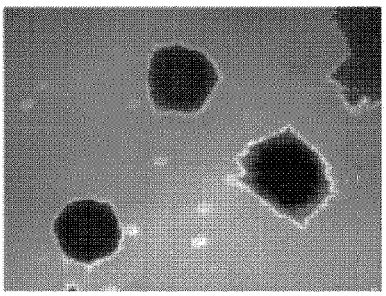 |

[Fig. 18]
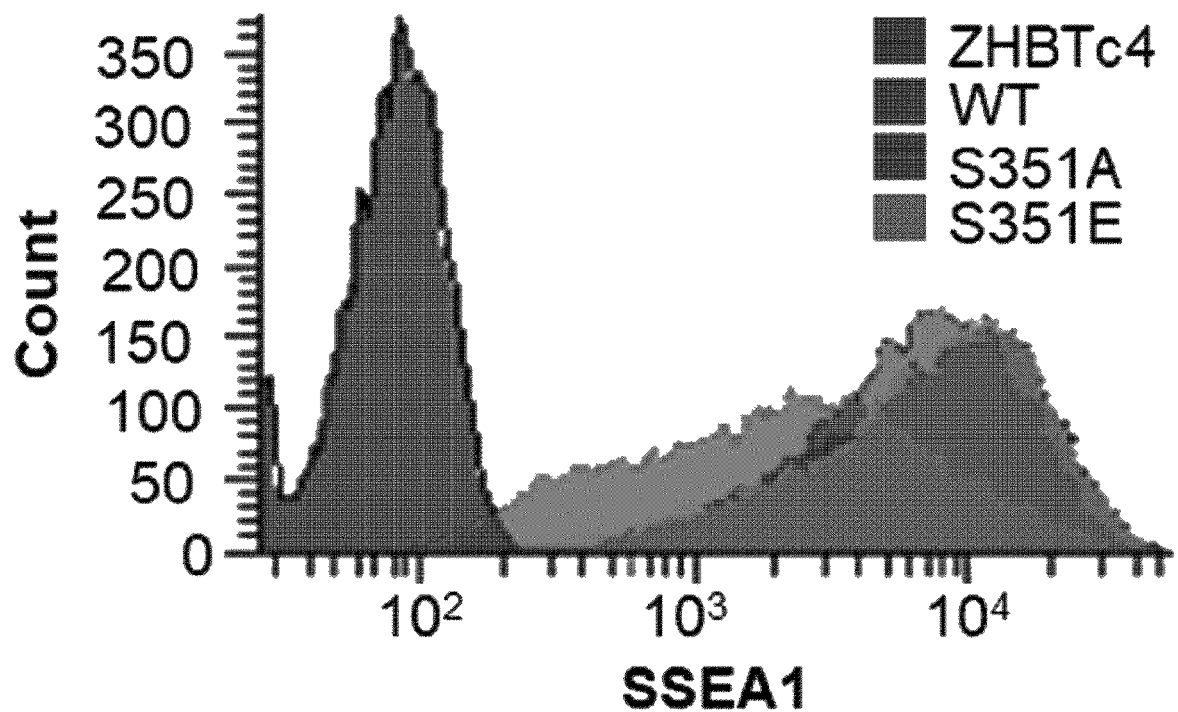

[Fig. 19]
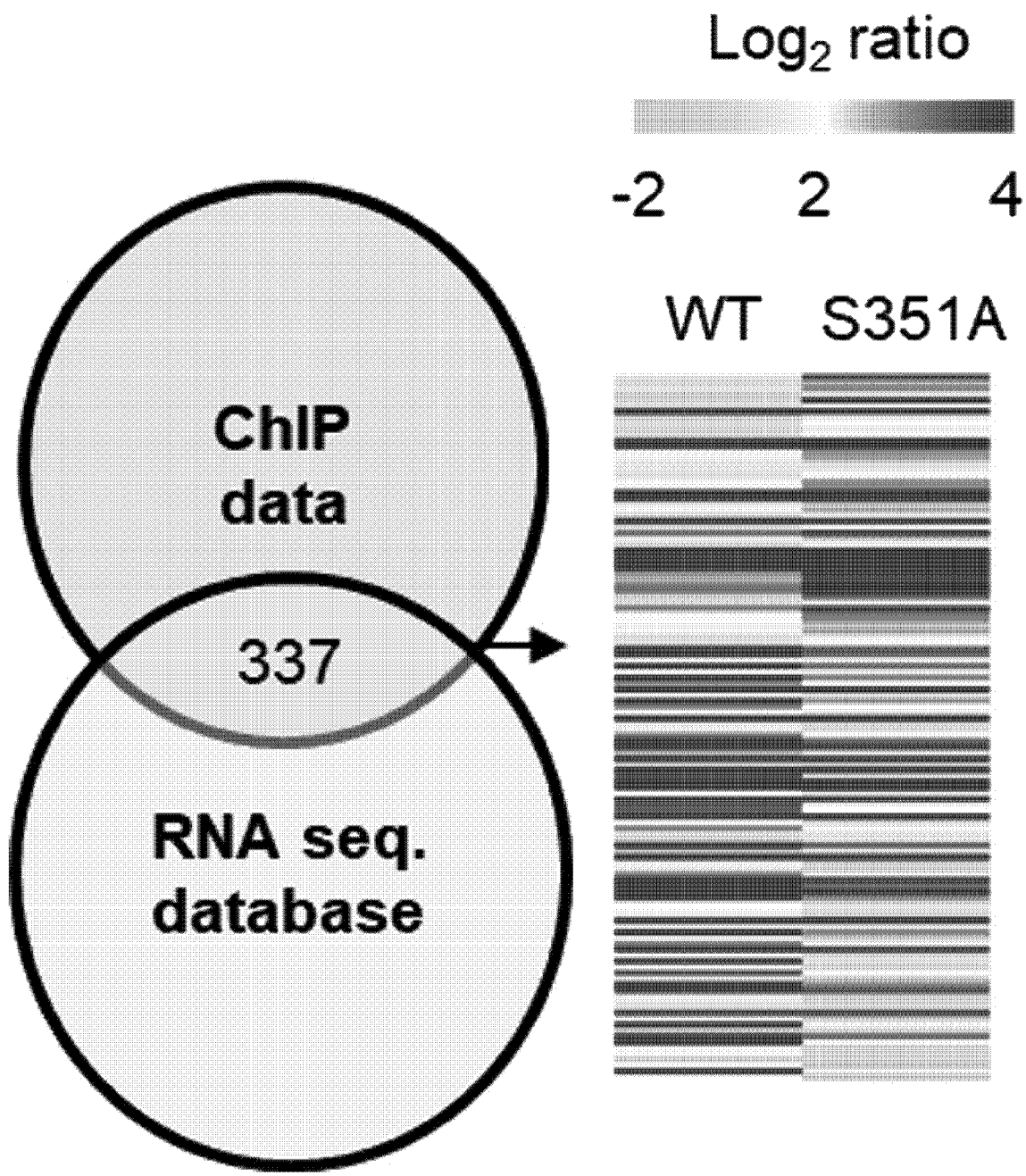

[Fig. 20]
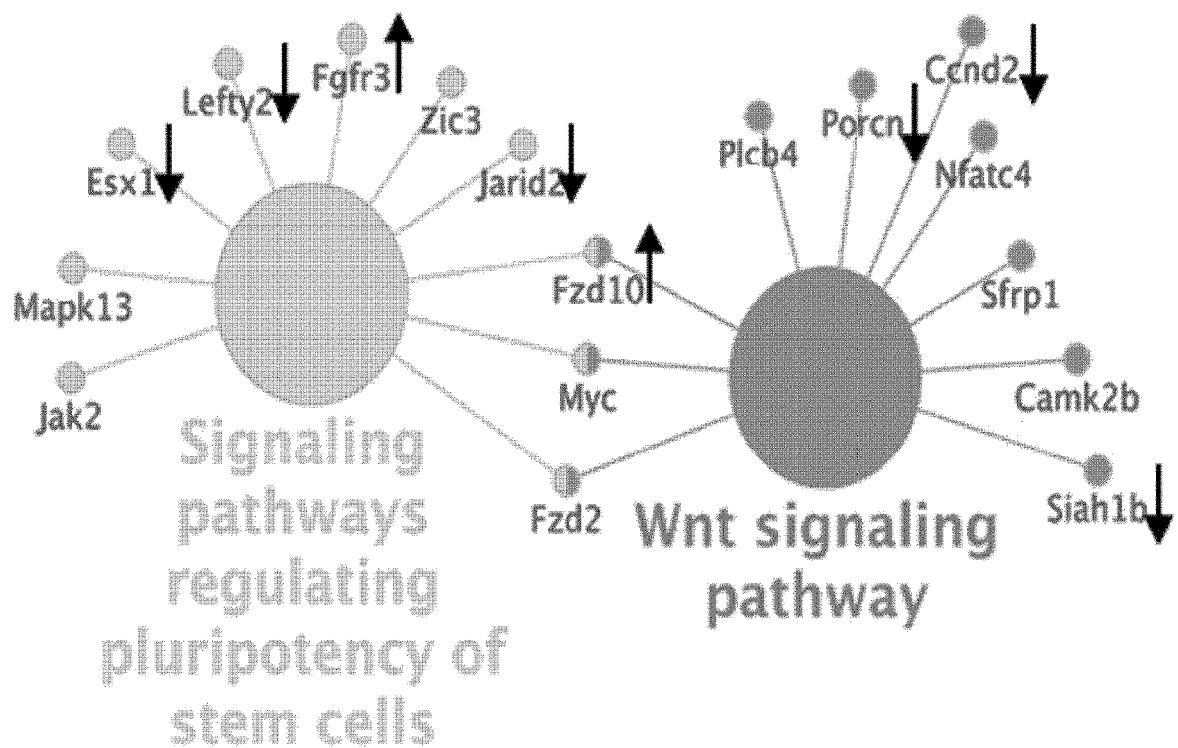

[Fig. 21]
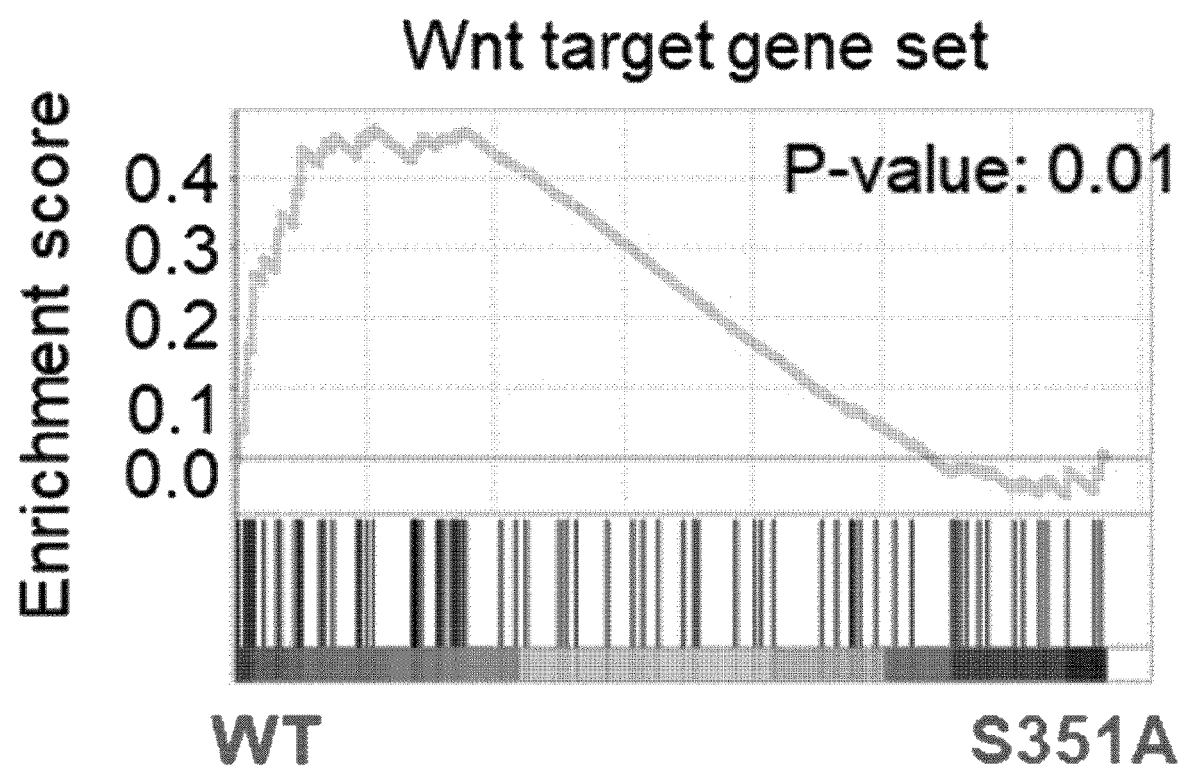

[Fig. 23]
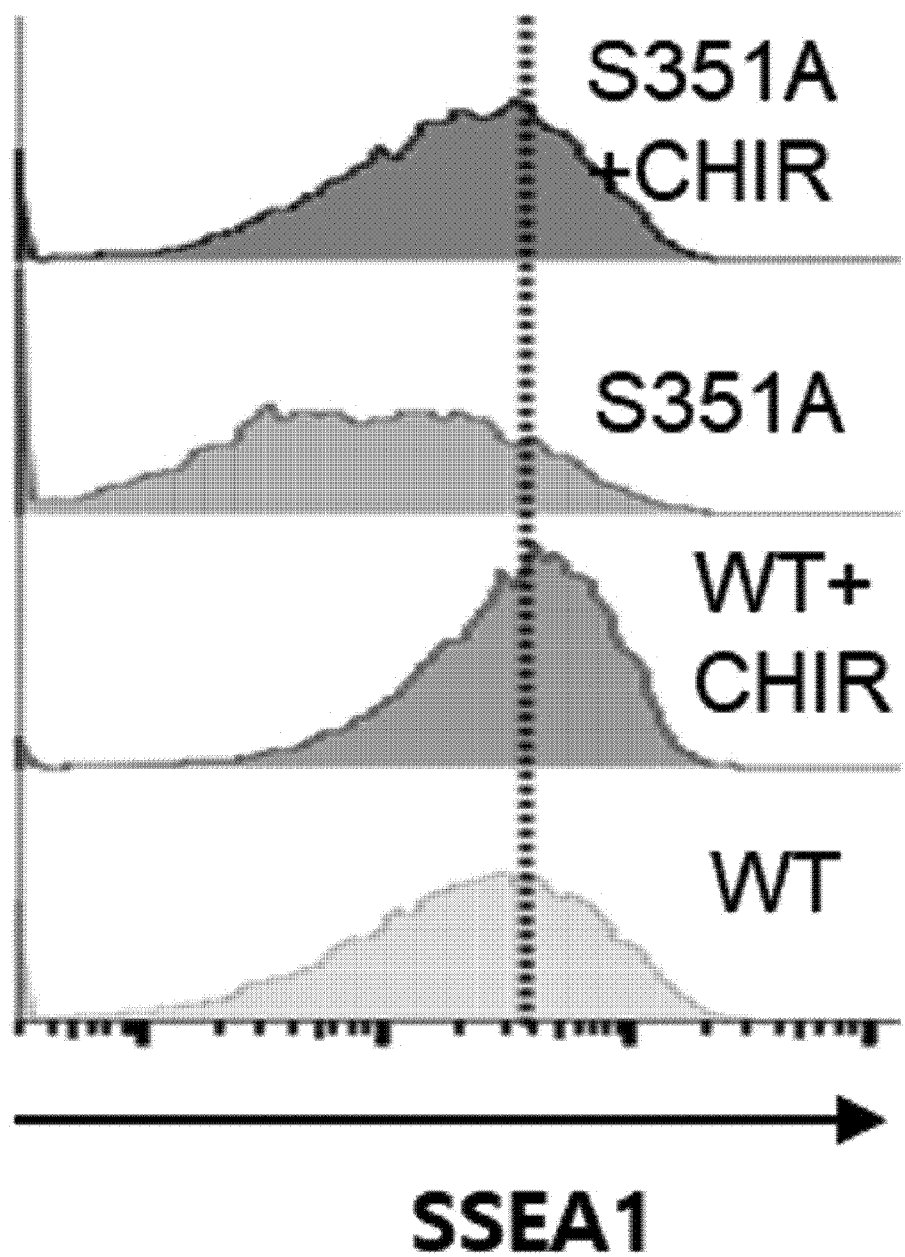

[Fig. 24]
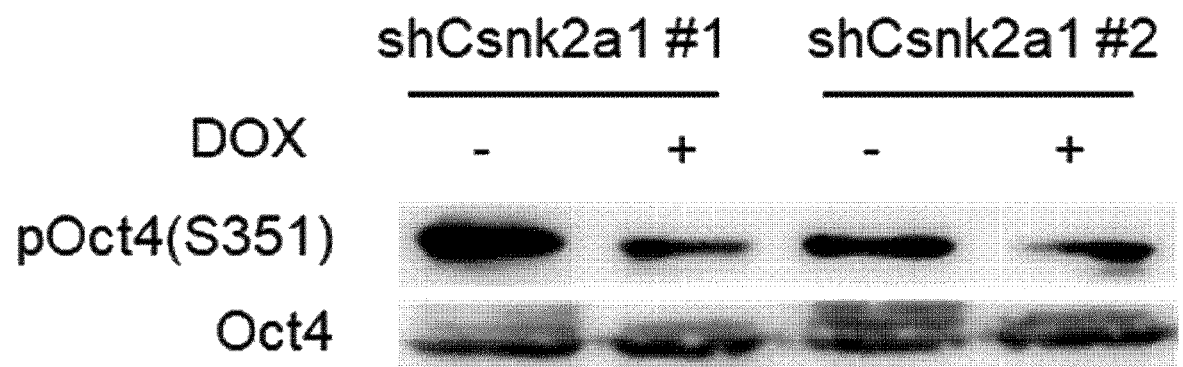

[Fig. 25]
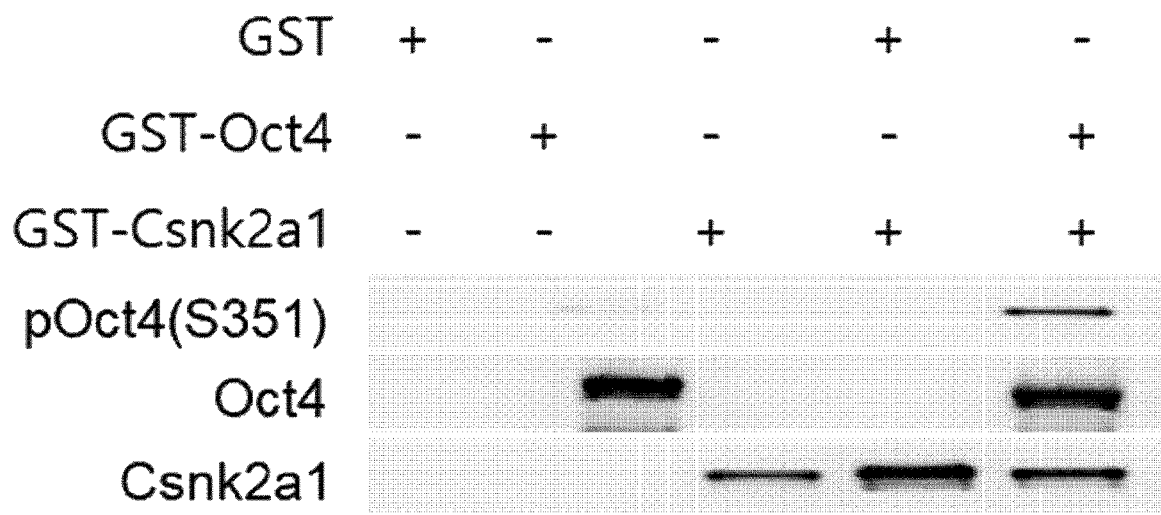

[Fig. 26]
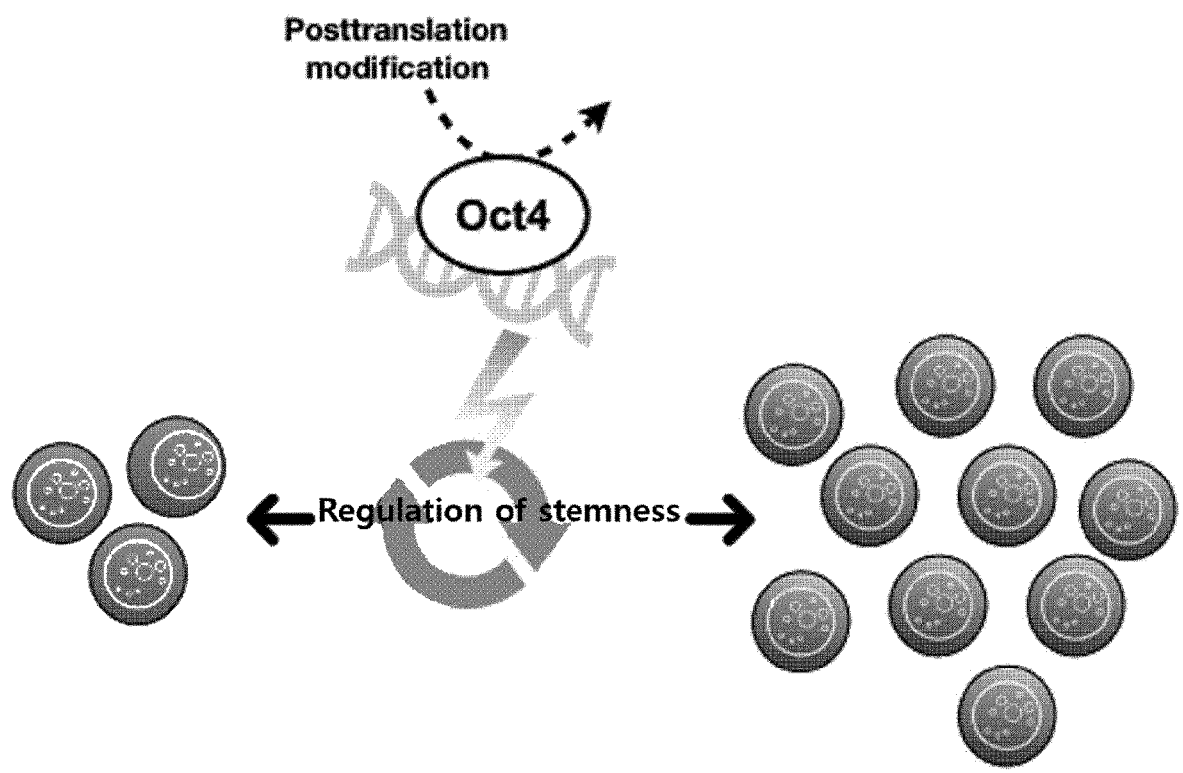

COMPOSITION COMPRISING MATERIAL FOR REGULATING OCT4 MODIFICATION TO REPRESS STEMNESS

TECHNICAL FIELD

The present invention relates to a composition comprising a material for regulating OCT4 modification to repress stemness.

BACKGROUND ART

Most anticancer agents which have been actively developed and substantially used in cancer treatment in recent years are drugs targeting cancer cells which are rapidly proliferated. According to anticancer treatment using these drugs, in an early stage, it seems that cancer cells are effectively killed to cure cancer, but eventually cancer stem cells still remaining in the body are not removed, and recurrence and/or metastasis of cancer actively happen, resulting in frequently caused problems of resistance to conventional cancer therapy. For this reason, recently, interest in cancer stem cells is increasing.

Cancer stem cells are cancer cells which possess an ability of unlimited self-renewal similar to normal stem cells but are slowly proliferated unlike normal cancer cells, and possess distinct abilities of stem cells to self-renew and differentiate, and they have been known to have different mechanisms from previously known cancer cells. Cancer stem cells, belonging to a specific subpopulation having a potential to differentiate into various cancer cell groups and self-renewal, exhibit drug and radiation resistances, resulting in recurrence or metastasis of cancer as well as initiation of cancer, and therefore inhibition of the proliferation of cancer stem cells is important for cancer treatment (Korean Unexamined Patent Application No. 10-2014-0143989).

In addition, since it is difficult for stem cell therapeutics which have been actively studied in recent years to regulate the proliferation or survival of stem cells, there are side effects. Typical side effects may be attributed to carcinogenesis of undifferentiated stem cells remaining in the body after treatment is finished.

Therefore, if there is a method of regulating the stemness of stem cells including cancer stem cells, it can be safely applied to various stem cell applications, and increase cancer therapeutic effects, thereby effectively inhibiting recurrence and metastasis of cancer and resistance.

Meanwhile, octamer-binding transcription factor 4 (OCT4), also known as POU5F1 (POU domain, class 5, transcription factor 1), is a transcription factor which is expressed in a conventional embryonic stem cell, serves to prevent cell differentiation and disappears when natural differentiation of cells begins. OCT4 is known as a marker specific for pluripotent embryonic stem cells.

However, in terms of cancer therapy, as conventionally known, beyond the use of OCT4 as a marker for detecting stemness, the relationship between regulation of OCT4 phosphorylation or methylation and regulation of Wnt signaling, such as regulation of stemness by directly regulating OCT4 itself by regulating the phosphorylation or methylation of a specific amino acid sequence among the amino acid sequence of OCT4, is not known yet. In addition, the relationship between regulation of OCT4 phosphorylation and Wnt signaling and regulation of stemness, for example, regulation of stemness by regulating Wnt signaling as well as regulating OCT4 phosphorylation, is not known yet.

DISCLOSURE OF INVENTION

Technical Problem

To solve the problems caused by conventional technology, the present invention is directed to provide a composition which includes a material, as an active ingredient, for repressing the stemness of stem cells and blocking Wnt signaling by regulating OCT4 phosphorylation or methylation so as to repress the stemness of various stem cells such as cancer stem cells.

However, technical problems to be solved in the present invention are not limited to the above-described problems, and other problems which are not described herein will be fully understood by those of ordinary skill in the art from the following descriptions.

Solution to Problem

To attain the object of the present invention, the present invention provides a composition which comprises a material for regulating OCT4 modification to repress the stemness of stem cells, wherein the OCT4 modification is regulated by any one or more selected from the group consisting of the following methods:

a) the phosphorylation of serine 281 in the amino acid sequence of mouse OCT4 or serine 288 in the amino acid sequence of human OCT4;

b) inhibition of the methylation of arginine 179 in the amino acid sequence of mouse OCT4, arginine 186 in the amino acid sequence of human OCT4, lysine 215 in the amino acid sequence of mouse OCT4, or lysine 222 in the amino acid sequence of human OCT4; and c) inhibition of the phosphorylation of serine 351 in the amino acid sequence of mouse OCT4 or serine 359 in the amino acid sequence of human OCT4.

According to an exemplary embodiment of the present invention, the composition may further comprise a material for blocking the activation of Wnt signaling.

According to another exemplary embodiment of the present invention, the amino acid sequence of the mouse OCT4 may be represented by an amino acid sequence of SEQ ID NO: 1.

According to still another exemplary embodiment of the present invention, the amino acid sequence of the human OCT4 may be represented by an amino acid sequence of SEQ ID NO: 2.

According to yet another exemplary embodiment of the present invention, the material may be any one selected from the group consisting of a peptide, a protein, a nucleotide and a compound.

According to yet another exemplary embodiment of the present invention, the material may comprise a material for inhibiting the expression of casein kinase 2 alpha 1 (CSNK2A1).

According to yet another exemplary embodiment of the present invention, the material for inhibiting CSNK2A1 expression may be a short hairpin RNA (shRNA) represented by a base sequence of SEQ ID NO: 5 or 6.

According to yet another exemplary embodiment of the present invention, the stem cells may be any one selected from the group consisting of embryonic stem cells, gametes, and cancer stem cells.

According to yet another exemplary embodiment of the present invention, the composition may inhibit proliferation, self-renewal, clustering, or survival of stem cells.

In addition, the present invention provides a kit for regulating the stemness of stem cells, which comprises a material for regulating modification of OCT4 and a material for activating Wnt signaling.

In addition, the present invention provides a cell therapeutic, which comprises a material for regulating modification of OCT4 and stem cells for cell therapy as active ingredients.

According to an exemplary embodiment of the present invention, the cell therapeutic may further comprise a material for blocking the activation of Wnt signaling.

According to another exemplary embodiment of the present invention, the cell therapeutic may inhibit metastasis, survival or carcinogenesis of stem cells for cell therapy.

In addition, the present invention provides a method of repressing stemness by regulating OCT4 modification in vitro, the method comprising any one or more selected from the group consisting of the following steps:

(a) phosphorylating serine 281 in the amino acid sequence of mouse OCT4 or serine 288 in the amino acid sequence of human OCT4;

(b) inhibiting the methylation of arginine 179 in the amino acid sequence of mouse OCT4, arginine 186 in the amino acid sequence of human OCT4, lysine 215 in the amino acid sequence of mouse OCT4, or lysine 222 in the amino acid sequence of human OCT4; and (c) inhibiting the phosphorylation of serine 351 in the amino acid sequence of mouse OCT4 or serine 359 in the amino acid sequence of human OCT4.

According to an exemplary embodiment of the present invention, the step (c) may further comprise blocking the activation of Wnt signaling.

In addition, the present invention provides a method of regulating stemness by regulating OCT4 modification in vitro, the method comprising: inhibiting the phosphorylation of serine 351 in the amino acid sequence of mouse OCT4 or serine 359 in the amino acid sequence of human OCT4; and activating Wnt signaling.

In addition, the present invention provides a pharmaceutical composition for preventing or treating cancer, the composition comprising: a material for regulating OCT4 modification.

According to an exemplary embodiment of the present invention, the pharmaceutical composition may further comprise an anticancer agent.

According to another exemplary embodiment of the present invention, the pharmaceutical composition may inhibit proliferation, survival, metastasis or recurrence of cancer, or resistance to an anticancer agent.

According to still another exemplary embodiment of the present invention, the pharmaceutical composition may further comprise a material for blocking the activation of Wnt signaling.

In addition, the present invention provides a method of preventing or treating cancer, the method comprising: administering the pharmaceutical composition into a subject.

In addition, the present invention provides a use of the pharmaceutical composition for preventing or treating cancer.

In addition, the present invention provides an antibody for detecting whether serine 351 in the amino acid sequence of mouse OCT4 or serine 359 in the amino acid sequence of human OCT4 is phosphorylated, and specifically, recognizing an epitope represented by an amino acid sequence of SEQ ID NO: 7 or 8 and specifically binding to phosphorylated serine 351 of mouse OCT4 or phosphorylated serine 359 of human OCT4.

In addition, the present invention provides a method of screening a material for repressing the stemness of stem cells, the method comprising the following steps:

(a) treating cells expressing mouse OCT4 or human OCT4 with a candidate material;

(b) detecting any one or more selected from the group consisting of the phosphorylation of serine 281 in the amino acid sequence of mouse OCT4 or serine 288 in the amino acid sequence of human OCT4, the methylation of arginine 179 in the amino acid sequence of mouse OCT4, arginine 186 in the amino acid sequence of human OCT4, lysine 215 in the amino acid sequence of mouse OCT4, or lysine 222 in the amino acid sequence of human OCT4, and the phosphorylation of serine 351 in the amino acid sequence of mouse OCT4 or serine 359 in the amino acid sequence of human OCT4; and (c) selecting the candidate material as a material for repressing the stemness of stem cells when serine 281 in the amino acid sequence of mouse OCT4 or serine 288 in the amino acid sequence of human OCT4 is phosphorylated, when the methylation of arginine 179 in the amino acid sequence of mouse OCT4, arginine 186 in the amino acid sequence of human OCT4, lysine 215 in the amino acid sequence of mouse OCT4, or lysine 222 in the amino acid sequence of human OCT4 is inhibited, or when the phosphorylation of serine 351 in the amino acid sequence of mouse OCT4 or serine 359 in the amino acid sequence of human OCT4 is inhibited.

According to an exemplary embodiment of the present invention, the screening method may comprise: detecting whether Wnt signaling is activated in cells as the step (b); and selecting the candidate material as a material for repressing the stemness of stem cells when the Wnt signaling is not activated as the step (c).

In addition, the present invention provides a method of imparting information for diagnosing whether the stemness of stem cells is repressed, the method comprising the following steps:

(a) detecting any one or more selected from the group consisting of the phosphorylation of serine 281 in the amino acid sequence of mouse OCT4 or serine 288 in the amino acid sequence of human OCT4, the methylation of arginine 179 in the amino acid sequence of mouse OCT4, arginine 186 in the amino acid sequence of human OCT4, lysine 215 in the amino acid sequence of mouse OCT4, or lysine 222 in the amino acid sequence of human OCT4, and the phosphorylation of serine 351 in the amino acid sequence of mouse OCT4 or serine 359 in the amino acid sequence of human OCT4 from cells expressing mouse OCT4 or human OCT4; and (b) determining that the stemness of stem cells is repressed when serine 281 in the amino acid sequence of mouse OCT4 or serine 288 in the amino acid sequence of human OCT4 is phosphorylated, when the methylation of arginine 179 in the amino acid sequence of mouse OCT4, arginine 186 in the amino acid sequence of human OCT4, lysine 215 in the amino acid sequence of mouse OCT4, or lysine 222 in the amino acid sequence of human OCT4 is inhibited, or when the phosphorylation of serine 351 in the amino acid sequence of mouse OCT4 or serine 359 in the amino acid sequence of human OCT4 is inhibited.

According to an exemplary embodiment of the present invention, the information imparting method may comprise: confirming whether Wnt signaling is activated in cells expressing mouse OCT4 or human OCT4 as the step (a); and determining that the stemness of stem cells is repressed when the Wnt signaling is not activated as the step (b).

In addition, the present invention provides a method of diagnosing whether the stemness of stem cells is repressed, the method comprising the following steps:

(a) detecting any one or more selected from the group consisting of the phosphorylation of serine 281 in the amino acid sequence of mouse OCT4 or serine 288 in the amino acid sequence of human OCT4, the methylation of arginine 179 in the amino acid sequence of mouse OCT4, arginine 186 in the amino acid sequence of human OCT4, lysine 215 in the amino acid sequence of mouse OCT4, or lysine 222 in the amino acid sequence of human OCT4, and the phosphorylation of serine 351 in the amino acid sequence of mouse OCT4 or serine 359 in the amino acid sequence of human OCT4; and (b) determining that the stemness of stem cells is repressed when serine 281 in the amino acid sequence of mouse OCT4 or serine 288 in the amino acid sequence of human OCT4 is phosphorylated, when the methylation of arginine 179 in the amino acid sequence of mouse OCT4, arginine 186 in the amino acid sequence of human OCT4, lysine 215 in the amino acid sequence of mouse OCT4, or lysine 222 in the amino acid sequence of human OCT4 is inhibited, or when the phosphorylation of serine 351 in the amino acid sequence of mouse OCT4 or serine 359 in the amino acid sequence of human OCT4 is inhibited.

According to an exemplary embodiment of the present invention, the diagnosing method may comprise:

confirming whether Wnt signaling is activated in cells expressing mouse OCT4 or human OCT4 as the step (a); and determining that the stemness of stem cells is repressed when the Wnt signaling is not activated as the step (b).

Advantageous Effects of Invention

A material for regulating OCT4 modification according to the present invention can regulate the phosphorylation or methylation of OCT4 and inhibit Wnt signaling, thereby effectively reducing the stemness of various stem cells. Therefore, since it can be effectively used in inhibition of proliferation, recurrence and metastasis of cancer, and inhibition of resistance to an anticancer agent, and can reduce stemness even in normal stem cells, the time for differentiation of embryonic stem cells into specific cells can be shortened, and efficiency can be increased. In addition, when the material for regulating OCT4 modification according to the present invention is used in cell therapy using embryonic stem cells, undifferentiated embryonic stem cells remaining after the therapy can be completely removed, and side effects generated in carcinogenesis can be effectively inhibited. For this reason, it is expected that the stability of cell therapy using embryonic stem cells can be significantly increased.

BRIEF DESCRIPTION OF DRAWINGS

FIG. 7 shows a result of confirming an effect of an OCT4 methylation-inhibited mutant on the self-renewal ability of stem cells in a transformed cell line according to an exemplary embodiment of the present invention with the formation of embryonic stem cell clusters using alkaline phosphatase staining.

FIG. 8 shows sequences of 14 amino acids including serine at the 351 position for designing OCT4 phosphorylation-specific antibodies according to an exemplary embodiment of the present invention.

FIG. 15 shows a result of confirming effects of an OCT4-serine 351 phosphorylation-inhibited mutant (S351A) and an OCT4-serine 351 phosphorylation-mimetic mutant (S351E) on self-renewal ability of stem cells in a transformed cell line according to an exemplary embodiment of the present invention with the formation of embryonic stem cell clusters using alkaline phosphatase staining.

FIG. 16 shows a result of confirming a transduced embryonic stem cell line according to an exemplary embodiment of the present invention using western blotting.

FIG. 17 shows a result of confirming the self-renewal ability of stem cells in a transduced embryonic stem cell line according to an exemplary embodiment of the present invention using alkaline phosphatase staining.

FIG. 18 shows a result of confirming self-renewal ability of stem cells in a transduced embryonic stem cell line according to an exemplary embodiment of the present invention with a difference in SSEA-1 expression.

FIG. 19 shows a result of analyzing a gene expression pattern and ChIP data of a transduced embryonic stem cell line according to an exemplary embodiment of the present invention.

FIG. 20 shows the result of FIG. 19 according to an exemplary embodiment of the present invention, visualized by analyzing signaling pathways.

FIG. 21 shows a result of amplification analysis of a gene set in response to Wnt signaling by the pathway analysis of FIG. 20 according to an exemplary embodiment of the present invention.

FIG. 23 shows a result of confirming the self-renewal ability of stem cells when Wnt signaling is artificially activated in a transduced embryonic stem cell line according to an exemplary embodiment of the present invention by SSEA-1 expression.

FIG. 24 shows a result of confirming that a kinase inducing OCT4 phosphorylation according to an exemplary embodiment of the present invention is casein kinase 2 alpha 1 (CSNK2A1).

FIG. 25 shows that CSNK2A1 as an in vitro kinase according to an exemplary embodiment of the present invention induces OCT4 phosphorylation.

FIG. 26 schematically shows that the self-renewal ability of stem cells is regulated by regulation of OCT4 modification (post-translational modification) according to an exemplary embodiment of the present invention.

BEST MODE FOR CARRYING OUT THE INVENTION

Figure 1:
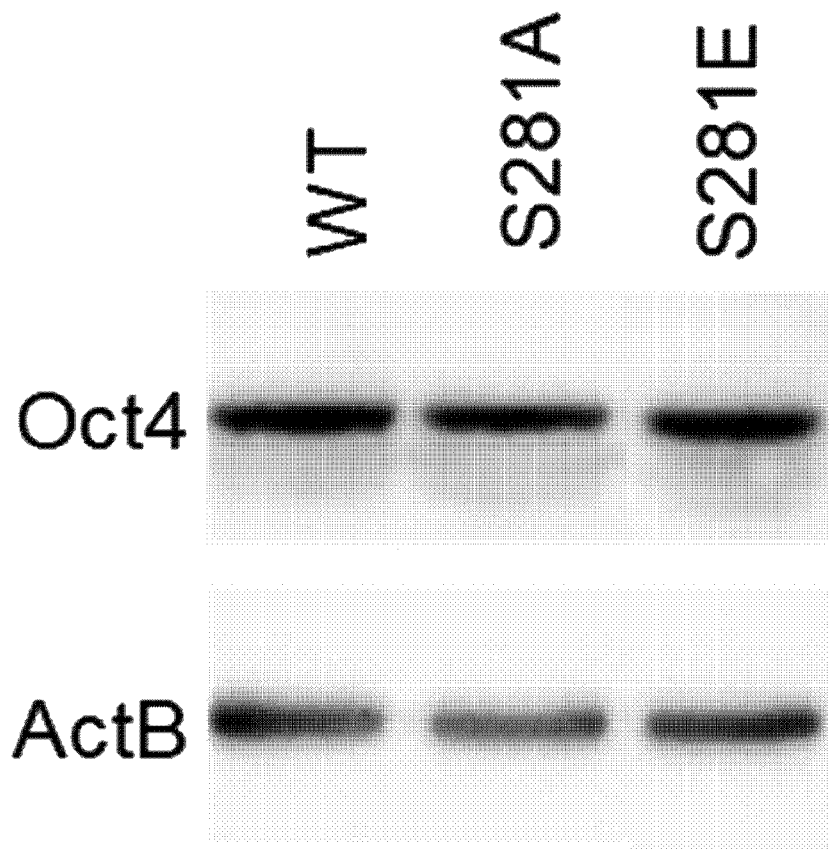
FIG. 1 shows a result of confirming that mutant OCT4 is expressed in a transformed cell line according to an exemplary embodiment of the present invention at an amount similar to wild type (WT).

The present invention provides a composition for repressing the sternness of stem cells, which comprises a material for regulating OCT4 modification, wherein
the OCT4 modification is regulated by any one or more selected from the group consisting of the following methods:
  a) the phosphorylation of serine 281 in the amino acid sequence of mouse OCT4 or serine 288 in the amino acid sequence of human OCT4;
  b) inhibition of the methylation of arginine 179 in the amino acid sequence of mouse OCT4, arginine 186 in the amino acid sequence of human OCT4, lysine 215 in the amino acid sequence of mouse OCT4, or lysine 222 in the amino acid sequence of human OCT4; and
  c) inhibition of the phosphorylation of serine 351 in the amino acid sequence of mouse OCT4 or serine 359 in the amino acid sequence of human OCT4.

According to the present invention, the composition may further comprise a material for blocking the activation of Wnt signaling.

According to the present invention, an amino acid sequence of the mouse OCT4 may be represented by an amino acid sequence of SEQ ID NO: 1 (NCBI Reference Sequence: NP_038661.2), and an amino acid sequence of the human OCT4 may be represented by an amino acid sequence of SEQ ID NO: 2 (NCBI Reference Sequence: NP_002692.2).

According to the present invention, the amino acid sequence of SEQ ID NO: 1 may be encoded by a base sequence of SEQ ID NO: 3 (NCBI Reference Sequence: NM_013633.3).

According to the present invention, the amino acid sequence of SEQ ID NO: 2 may be encoded by a base sequence of SEQ ID NO: 4 (NCBI Reference Sequence: NM_002701.5).

According to the present invention, the material may be any one selected from the group consisting of a peptide, a protein, a nucleotide and a compound, and preferably a material for inhibiting CSNK2A1 expression, and the material for inhibiting CSNK2A1 expression may include a short hairpin RNA (shRNA) represented by a base sequence of SEQ ID NO: 5 or 6, and may be any material capable of regulating OCT4 modification without limitation.

The term "OCT4" used herein is a member of the family of POU transcription factors and expressed in pluripotent embryonic stem cells and gametes. Members of the POU transcription factor family have conserved DNA-binding domains, that is, POU domains, and the domains were first identified in Pit-1, Oct-1, Oct-2 and Unc-86 among the transcription factors. OCT4 activates transcription by an octamer motif which is adjacent to or spaced apart from a transcription initiation site.

The term "Wnt" used herein is a secreted glycoprotein, and a ligand for a 7-transmembrane receptor, Frizzled, and a conjugated receptor, 1-transmembrane lowdensity lipid protein receptor-associated protein 5,6 (LRPS/6). The Wnt gene family encodes a large set of secreted proteins associated with Int1/Wnt1 proto-oncogenes and *Drosophila* wingless (Wg), which is a homologous gene of *Drosophila* Wnt1. Wnt is expressed in various tissues and organs, and plays a pivotal role in segmentation in *drosophila*; endodermal development in *C. elegans*; and a variety of development processes including establishment of limb polarity, neural differentiation, kidney morphogenesis, sex determination and brain development in mammals. The Wnt signaling pathway is conserved in species ranging from nematoda, drosophila to mammals, and an important regulator for animal development in embryonic development and mature organisms.

The term "stem cells" used herein is the generic term for undifferentiated cells having an ability to differentiate into various types of tissue cells, that is, stemness. These stem cells are largely divided into embryonic stem cells, which can be produced using an embryo, adult stem cells, gametes, and cancer stem cells, and the embryonic stem cells refer to the stage of a cell mass before a specific organ only aged less than 14 days after fertilization is formed, and recently, the embryonic stem cells are also produced from normal cells through reprogramming. Accordingly, the stem cell is any cell that can differentiate into all cells and tissues constituting a body without limitation. Adult stem cells are extracted from umbilical cord blood, bone marrow, blood, etc., and refer to primitive cells just before differentiating into cells of a specific organ such as bone, liver, blood or the like. Gametes are cells that transfer genetic information to the next generation through reproduction, and include sperm and eggs in humans, but the present invention is not limited thereto. In addition, the stem cells are cells that can maintain a new stem cell in a cluster through self-renewal in a process of producing a cell cluster by forming clones, and have an ability to form one or more types of specific cells through differentiation.

The term "stemness" used herein refers to the characteristic ability of stem cells, which includes multipotency and unipotency as well as pluripotency which can differentiate into all types of cells constituting an organism such as nerves, blood, cartilage, etc., and the stemness also includes an ability to self-replicate or self-renew. It also means that stem cells have an ability to form a cluster through self-replication or self-renewal. In this case, the stemness may include an ability to differentiate into various types of cells from embryonic stem cells obtained from an embryo generated from a fertilized egg, and while there is a difference in the functional aspect, also include an ability to differentiate into various types of cells from adult stem cells conserved in each tissue of an adult body.

Cancer stem cells generically refer to cancer cells having stemness, which is the distinct ability of stem cells, such as self-renewal or differentiation. Cancer stem cells, unlike general cancer cells, are generally grown slowly or maintained in a dormant state, such that they have resistance to an anticancer agent under normal tumor growth conditions (refers to a state without cell stress since there are sufficient nutrients (glucose) required for cell growth and an abundant tumor microenvironment), and for example, the cancer stem cells may be different from general cancer cells in terms of the function of a key material for regulating metabolism since expression of a transcription-regulating factor such as PGC-1α is controlled unlike normal tumor cells. Cancer stem cells encompass cells having infiltrating and metastatic abilities, acquiring resistance to apoptosis in a nutrient-deficient state through such different metabolism-regulating abilities and regulation of cell signal transduction pathways metabolically associated therewith. However, there is no limitation as long as cells can differentiate into general cancer cells.

In the present invention, the stem cells may be any one selected from the group consisting of embryonic stem cells, gametes, and cancer stem cells, but there is no limitation as long as cells are a type of stem cells expressing an OCT4 protein.

In the present invention, the composition may repress the stemness of stem cells, such that proliferation, self-renewal, a clustering ability or survival of stem cells can be inhibited, and therefore the composition can be used in all fields using regulation of stem cells.

In addition, the present invention provides a kit for regulating the stemness of stem cells, which comprises a material for regulating OCT4 modification and a material for activating Wnt signaling.

Here, the kit comprising a material for regulating OCT4 modification and a material for activating Wnt signaling may regulate the stemness of stem cells by repressing the stemness by inhibiting the activation of Wnt signaling by inhibiting the phosphorylation of serine 351 in the amino acid sequence of mouse OCT4 or serine 359 in the amino acid sequence of human OCT4 by an OCT4 modification-regulating material, and by increasing the stemness again by activating only Wnt signaling by the material for activating Wnt signaling in the OCT4 phosphorylation-inhibited cells. To regulate stemness as described above, each of the OCT4 modification-regulating material and the material for activating Wnt signaling may be applied one or more times without limitation, and there is no limitation to the order of applying these materials, and thus, the materials may be applied simultaneously or separately.

In the present invention, the kit may include a container; a protocol; a material for regulating OCT4 modification; and a material for activating Wnt signaling. The container may serve to package each of the material for regulating OCT4 modification and the material for activating Wnt signaling, and to store and fix these materials. The container may be formed of, for example, plastic or glass, but the present invention is not limited thereto. In addition, the protocol included in the kit for regulating the stemness of stem cells according to the present invention may contain instructions for regulating the stemness of stem cells. The instructions may be described in a separate sheet or booklet, other than the container, and the sheet or booklet may be included in addition to the material for regulating OCT4 modification and the material for activating Wnt signaling in the container.

In addition, the present invention provides a cell therapeutic, which comprises the material for regulating OCT4 modification and stem cells for cell therapy as active ingredients.

In the present invention, the cell therapeutic may further comprise a material for blocking the activation of Wnt signaling.

The term "cell therapeutic" used herein refers to a drug used in treatment, diagnosis and prevention by a series of methods for proliferating or selecting autologous, allogenic or xenogenic living cells in vitro to restore the function of cells or tissue, or changing biological characteristics of cells by different methods.

In the present invention, the cell therapeutic may regulate stem cells by inhibiting metastasis or survival of therapeutic stem cells, or preventing cancer caused by carcinogenesis of therapeutic stem cells remaining after treatment. However, there is no limitation as long as a cell therapeutic has an effect induced by inhibition of the OCT4 function.

In addition, the present invention provides a method of repressing stemness by regulating OCT4 modification in vitro, which comprises any one or more selected from the group consisting of the following steps:

(a) the phosphorylation of serine 281 in the amino acid sequence of mouse OCT4 or serine 288 in the amino acid sequence of human OCT4;

(b) inhibition of the methylation of arginine 179 in the amino acid sequence of mouse OCT4, arginine 186 in the amino acid sequence of human OCT4, lysine 215 in the amino acid sequence of mouse OCT4, or lysine 222 in the amino acid sequence of human OCT4; and (c) inhibition of the phosphorylation of serine 351 in the amino acid sequence of mouse OCT4 or serine 359 in the amino acid sequence of human OCT4.

In the present invention, the step (c) may further comprise blocking the activation of Wnt signaling.

In addition, the present invention provides a method of regulating stemness by regulating OCT4 modification in vitro, which comprises: inhibiting the phosphorylation of serine 351 in the amino acid sequence of mouse OCT4 or serine 359 in the amino acid sequence of human OCT4; and activating Wnt signaling.

In addition, the present invention provides a pharmaceutical composition for preventing or treating cancer, which comprises the material for regulating OCT4 modification.

In addition, the present invention provides a method of preventing or treating cancer, which comprises administering the pharmaceutical composition into a subject.

In addition, the present invention provides a use of the pharmaceutical composition for preventing or treating cancer.

The term "cancer" used herein refers to the generic term for diseases caused by aggressive cells which ignore the limit to normal growth of cells, divided and grown, invasive cells which infiltrate into surrounding tissues, and metastatic cells which spread to other sites in the body.

The main causes of cancerous death are metastasis of cancer and therapeutic resistance, and recently, it has been strictly proven that its fundamental cause is cancer cells having stemness. Therefore, it is expected that an anticancer strategy for reducing stemness of cancer cells leads to a substantial decrease in death caused by cancer.

There are two major pathways in which cancer cells acquire stemness: one is carcinogenesis of normal stem cells; and the other is reprogramming of cancer cells. It has been reported that, in cancer patients, particularly, key factors of embryonic stem cells play an important role in maintaining the stemness of cancer cells, and as malignancy of cancer progresses, expression of an embryonic stem cell-related gene family, rather than normal tissue stem cell-related genes, is increased.

The term "modification" used herein refers that a specific moiety binds to a residue of an amino acid after protein synthesis (the process of translating mRNA transcribed from DNA and synthesizing a primary chain of amino acids). In the present invention, the protein modification moiety may be selected from the group consisting of acylation, alkylation, amidation, butyrylation, carboxylation, glycosylation, formylation, hydroxylation, iodination, oxidation, phosphorylation, propionylation, succinylation, sulfation, glycation, carbonylation, ubiquitination, sumoylation, neddylation and pupylation moieties. In addition, the alkylation can be any chemical reaction for producing an atomic group from which one hydrogen atom is removed from an aliphatic saturated hydrocarbon, selected from the group consisting of methylation, acetylation, ethylation, propylation, amylation, hexylation, heptylation, octylation, nonylation and decylation. In the present invention, the modification moiety may be a phosphorylation or methylation moiety, but the present invention is not limited thereto.

The term "phosphorylation" used herein is a biochemical reaction which adds a phosphate group to a serine (S), threonine (T) or tyrosine (Y) residue of a specific protein, which is catalyzed by a protein kinase. Phosphorylation conventionally changes the function of a target protein to regulate activity of the protein. As a part of the mechanisms of cell homeostasis, phosphorylation is merely a temporary process, and reversed by other enzymes called phosphatases. Any unusual events in an aspect of the reaction (phosphorylation vs. dephosphorylation) may destroy a cell function.

The term "methylation" used herein is broadly classified into DNA methylation and histone methylation. DNA methylation is binding of a methyl group to the carbon no. 5 of a cytosine base in the nucleotide 5'-CpG-3', and uses a DNA methyltransferase as an enzyme. Meanwhile, histone methylation is binding of a methyl group to a residue of an amino acid, such as arginine (R) or lysine (K), of histone H3 or histone H4. Histone methylation inhibits or activates transcription depending on whether methylation occurs at any residue of arginine or lysine. The arginine residue may be methylated with monomethyl arginine or dimethylarginine by peptidyl arginine methyltransferase (PRMT), in which the dimethylarginine may have an asymmetric structure in which two methyl groups bind to one nitrogen atom or a symmetric structure in which a methyl group binds to each of two nitrogen atoms. Even three methyl groups may bind to a lysine residue by lysine methyltransferase.

According to an exemplary embodiment of the present invention, as a result of confirming the relationship between the phosphorylation of serine 281 of mouse OCT4 and OCT4 activation, it is confirmed that the number of embryonic stem cells forming clusters is increased in a OCT4-serine 281 phosphorylation-inhibited mutant cell line (S281A), compared with a wild type, whereas the number of clusters is decreased in a OCT4-serine 281 phosphorylation-mimetic mutant cell line (S281E), compared with the wild type, which shows that, when serine 281 of mouse OCT4 (serine 288 of human OCT4) is phosphorylated, stemness is reduced (refer to Example 1).

According to another exemplary embodiment of the present invention, to confirm a new methylation site of OCT4, an OCT4 protein is analyzed using a mass spectrometer after being isolated and purified from mouse embryonic stem cells, and thereby it is confirmed that new methylation occurs at arginine 179 of mouse OCT4 (arginine 186 of human OCT4) and lysine 215 of mouse OCT4 (lysine 222 of human OCT4), which were previously unknown (refer to Example 2-1).

According to still another exemplary embodiment of the present invention, as a result of confirming the relationship between OCT4 methylation and OCT4 activation, it is confirmed that the number of embryonic stem cells forming a cluster is decreased in OCT4 methylation-inhibited mutant cell lines (R179K and K215R), compared with a wild type, confirming that, when the methylation of mouse arginine 179 (arginine 186 of human OCT4) or lysine 215 of mouse OCT4 (lysine 222 of human OCT4) is inhibited, stemness is reduced (refer to Example 2-2).

According to yet another exemplary embodiment of the present invention, it is confirmed that an antibody specifically recognizing the phosphorylation of serine 351 of OCT4 is produced (refer to Example 3-1), and the phosphorylation of serine 351 of mouse OCT4 is also detected in human cancer cells (NCCIT and NTERA2) (refer to Example 3-2).

According to yet another exemplary embodiment of the present invention, as a result of confirming the relationship between the phosphorylation of serine 351 of OCT4 and OCT4 activation, it is confirmed that the number of embryonic stem cells forming clusters is decreased in a OCT4-serine 351 phosphorylation-inhibited mutant cell line (S351A), compared with a wild type, whereas the number of clusters is increased in a OCT4-serine 351 phosphorylation-mimetic mutant cell line (S351E), compared with the wild type, which shows that, when the phosphorylation of mouse serine 351 of OCT4 (serine 359 of human OCT4) is inhibited, stemness is reduced (refer to Example 3-3).

Accordingly, the OCT4 modification-regulating material according to the present invention inhibits the function of OCT4 through the phosphorylation of serine 281 of mouse OCT4 or serine 288 of human OCT4; inhibition of the methylation of arginine 179 of mouse OCT4, arginine 186 of human OCT4, lysine 215 of mouse OCT4, or lysine 222 of human OCT4; or inhibition of the phosphorylation of serine 351 of mouse OCT4 or serine 359 of human OCT4, such that normal stem cells lose stemness and become differentiated, cancer cells lose stemness, making it impossible to survive for a long time, and cancer does not recur after anticancer therapy.

According to yet another exemplary embodiment of the present invention, as a result of confirming the relationship between OCT4 phosphorylation and regulation of Wnt signaling, it is confirmed that, when phosphorylation-inhibited mutant (S351A) OCT4 is expressed, Wnt signaling is inhibited, and when Wnt signaling is artificially activated in cells stably expressing phosphorylation-inhibited mutant OCT4, the self-renewal ability of stem cells is restored (refer to Example 4).

According to yet another exemplary embodiment of the present invention, as a result of confirming a kinase inducing the phosphorylation of serine 351 of OCT4, it is confirmed that CSNK2A1 induces the phosphorylation of serine 351 of OCT4 (refer to Example 5).

In the present invention, the cancer may be OCT4-associated cancer, preferably including thyroid cancer, cervical cancer, brain cancer, lung cancer, ovarian cancer, liver cancer, pancreatic cancer, prostate cancer, skin cancer, tongue cancer, breast cancer, uterine cancer, gastric cancer, rectal cancer, colorectal cancer or hematological cancer, and more preferably including gastric cancer, colorectal cancer, lung cancer, liver cancer, prostate cancer, breast cancer, cervical cancer or ovarian cancer, but the present invention is not limited thereto.

The term "prevention" used herein refers to all actions for inhibiting a disease such as cancer or delaying the onset thereof by administration of the pharmaceutical composition according to the present invention.

The term "treatment" used herein refers to all actions involved in alleviating or beneficially changing symptoms of a disease such as cancer by administration of the pharmaceutical composition according to the present invention.

The term "administration" used herein refers to providing the composition of the present invention to a subject by a suitable method.

The term "subject" used herein refers to a subject in need of treatment and to which the composition of the present invention may be administered, and more specifically, a mammal such as a human, or a non-human primate, a mouse, a dog, a cat, a horse or a cow.

The term "pharmaceutical composition" used herein is prepared for the purpose of prevention or treatment of cancer, and may be used by preparation in various formulations according to a conventional method. For example, the pharmaceutical composition may be prepared in an oral formulation such as a powder, a granule, a tablet, a capsule, a suspension, an emulsion or a syrup, a medication for topical use such as a cream, a gel, a patch, a spray, an ointment, a plaster, a lotion, a liniment, a paste or a cataplasma, a suppository or a sterilized injection.

The pharmaceutical composition according to the present invention may further include a suitable carrier, an excipient or a diluent, which are conventionally used in preparation of a pharmaceutical composition. Here, examples of a carrier, excipient and diluent which can be included in the composition may include lactose, dextrose, sucrose, an oligosaccharide, sorbitol, mannitol, xylitol, erythritol, maltitol, starch, acacia gum, alginate, gelatin, calcium phosphate, calcium silicate, cellulose, methyl cellulose, microcrystalline cellulose, polyvinyl pyrrolidone, water, methylhydroxybenzoate, propylhydroxybenzoate, talc, magnesium stearate and mineral oil. In preparation, the composition is formulated using a diluent or an excipient such as a filler, a thickening agent, a binder, a wetting agent, a disintegrant, a surfactant, which are generally used. A solid formulation for oral administration may be a tablet, pill, powder, granule or capsule, and such a solid formulation may be prepared by mixing at least one of excipients, for example, starch, calcium carbonate, sucrose, lactose and gelatin with the extract. Also, in addition to the simple excipient, lubricants such as magnesium stearate and talc may also be used. As a liquid formulation for oral administration, a suspension, a liquid for internal use, an emulsion, or a syrup may be used, and a generally-used simple diluent such as water or liquid paraffin, as well as various types of excipients, for example, a wetting agent, a sweetener, a fragrance and a preservative may be included. A formulation for parenteral administration includes a sterilized aqueous solution, a non-aqueous solvent, a suspension, an emulsion, a lyophilizing agent and a suppository. As the non-aqueous solvent or suspension, propylene glycol, polyethylene glycol, a vegetable oil such as olive oil, or an injectable ester such as ethyl oleate may be used. As a suppository base, Witepsol, Tween 61, cacao butter, laurin fat or glycerogelatin may be used.

The pharmaceutical composition of the present invention may be administered orally or parenterally (e.g., intravenously, subcutaneously, intraperitoneally or locally) depending on a desired method, and a dose of the pharmaceutical composition may vary depending on the condition and body weight of a patient, the severity of a disease, a drug type, an administration route and time, and may be suitably selected by one of ordinary skill in the art.

The pharmaceutical composition of the present invention is administered at a pharmaceutically effective amount. The "pharmaceutically effective amount" used herein refers to an amount sufficient for treating a disease at a reasonable benefit/risk ratio applicable for medical treatment, and an effective dosage may be determined by parameters including a type of a patient's disease, severity, drug activity, sensitivity to a drug, administration time, an administration route and an excretion rate, the duration of treatment and drugs simultaneously used, and other parameters well known in medical fields. The pharmaceutical composition of the present invention may be administered separately or in combination with other therapeutic agents, and may be administered in single or multiple doses. In consideration of all of the above-mentioned parameters, it is important to achieve the maximum effect with the minimum dose without a side effect, and such a dose may be easily determined by one of ordinary skill in the art. Administration may be performed one or several times per day.

In the present invention, the pharmaceutical composition may further comprise an anticancer agent, which is preferably doxorubicin, cisplatin, gemcitabine, oxaliplatin or 5-FU, and the compound is not limited as long as it can be used as an anticancer agent.

In the present invention, the pharmaceutical composition may repress the stemness of cancer stem cells, thereby inhibiting proliferation, survival, metastasis or recurrence of cancer or resistance to an anticancer agent, but the pharmaceutical composition is not limited as long as it can exhibit an effect attributed to the repression of the stemness of cancer stem cells.

In the present invention, the pharmaceutical composition may further comprise a material for blocking the activation of Wnt signaling.

In addition, the present invention provides an antibody for detecting the phosphorylation of serine 351 in the amino acid sequence of mouse OCT4 or serine 359 in the amino acid sequence of human OCT4, which recognizes an epitope represented by an amino acid sequence of SEQ ID NO: 7 or 8 and specifically binds to phosphorylated serine 351 of mouse OCT4 or phosphorylated serine 359 of human OCT4.

The term "antibody" used herein refers to a polypeptide including an immunoglobulin gene specifically binding to and recognizing an antibody or a framework region derived from a fragment thereof. The recognized immunoglobulin gene includes numerous immunoglobulin variable domain genes, in addition to κ, λ, α, γ, δ, ε and μ constant domain genes. A light chain is classified as κ or λ, and a heavy chain is classified as γ, μ, α, δ, or ε, designating an immunoglobulin as IgG, IgM, IgA, IgD or IgE. Typically, an antigen-binding site on an antibody is the most critical in terms of binding specificity and affinity. In some embodiments, an antibody or an antibody fragment may be derived from a different organism such as a human, a mouse, a rat, a hamster, a rabbit, a camel, etc.

In the present invention, an antibody for detecting the phosphorylation of serine 351 in the amino acid sequence of mouse OCT4 or serine 359 in the amino acid sequence of human OCT4 may be a polyclonal antibody derived from a rabbit, but the present invention is not limited thereto, and an epitope recognized by the antibody may be represented by the amino acid sequence of SEQ ID NO: 7 or 8.

In addition, the present invention provides a method of screening a material for repressing the stemness of stem cells, which comprises the following steps:

(a) treating cells expressing mouse OCT4 or human OCT4 with a candidate material;

(b) detecting any one or more selected from the group consisting of the phosphorylation of serine 281 in the amino acid sequence of mouse OCT4 or serine 288 in the amino acid sequence of human OCT4, the methylation of arginine 179 in the amino acid sequence of mouse OCT4, arginine 186 in the amino acid sequence of human OCT4, lysine 215 in the amino acid sequence of mouse OCT4, or lysine 222 in the amino acid sequence of human OCT4, and the phosphorylation of serine 351 in the amino acid sequence of mouse OCT4 or serine 359 in the amino acid sequence of human OCT4; and (c) selecting the candidate material, as a material for repressing the stemness of stem cells, when serine 281 in the amino acid sequence of mouse OCT4 or serine 288 in the amino acid sequence of human OCT4 is phosphorylated, when the methylation of arginine 179 in the amino acid sequence of mouse OCT4, arginine 186 in the amino acid sequence of human OCT4, lysine 215 in the amino acid sequence of mouse OCT4, or lysine 222 in the amino acid sequence of human OCT4 is inhibited, or when the phosphorylation of serine 351 in the amino acid sequence of mouse OCT4 or serine 359 in the amino acid sequence of human OCT4 is inhibited.

In the present invention, the screening method may comprise detecting whether Wnt signaling is activated in cells as the step (b); and selecting the candidate material as a material for repressing the stemness of stem cells when the Wnt signaling is not activated as the step (c).

In addition, the present invention provides a method of screening a material for screening a material for repressing the stemness of stem cells, which comprises the following steps:

(a) treating cells expressing mouse OCT4 or human OCT4 with a candidate material;

(b) confirming whether Wnt signaling is activated in the cells; and (c) selecting the candidate material as a material for repressing the stemness of stem cells when Wnt signaling is not activated in the step (b).

In the present invention, the candidate material may be a nucleotide, DNA, RNA, an amino acid, an aptamer, a protein, a compound, a natural substance or a natural extract, and the candidate material is not limited as long as it can be used for the repression of the stemness of stem cells.

In addition, the present invention provides a method of imparting information for diagnosing whether the stemness of stem cells is repressed, the method comprising the following steps:

(a) detecting any one or more selected from the group consisting of the phosphorylation of serine 281 in the amino acid sequence of mouse OCT4 or serine 288 in the amino acid sequence of human OCT4, the methylation of arginine 179 in the amino acid sequence of mouse OCT4, arginine 186 in the amino acid sequence of human OCT4, lysine 215 in the amino acid sequence of mouse OCT4, or lysine 222 in the amino acid sequence of human OCT4, and the phosphorylation of serine 351 in the amino acid sequence of mouse OCT4 or serine 359 in the amino acid sequence of human OCT4 from cells expressing mouse OCT4 or human OCT4; and (b) determining that the stemness of stem cells is repressed when serine 281 in the amino acid sequence of mouse OCT4 or serine 288 in the amino acid sequence of human OCT4 is phosphorylated, when the methylation of arginine 179 in the amino acid sequence of mouse OCT4, arginine 186 in the amino acid sequence of human OCT4, lysine 215 in the amino acid sequence of mouse OCT4, or lysine 222 in the amino acid sequence of human OCT4 is inhibited, or when the phosphorylation of serine 351 in the amino acid sequence of mouse OCT4 or serine 359 in the amino acid sequence of human OCT4 is inhibited.

In the present invention, the method of imparting information may comprise:

confirming whether Wnt signaling is activated in cells expressing mouse OCT4 or human OCT4 as the step (a); and determining that the stemness of stem cells is repressed when the Wnt signal is not activated as the step (b).

In addition, the present invention provides a method of imparting information for diagnosing whether the stemness of stem cells is repressed, the method comprising the following steps:

(a) confirming whether Wnt signaling is activated in cells expressing mouse OCT4 or human OCT4; and (b) determining that the stemness of stem cells is repressed when the Wnt signal is not activated in the step (a).

In addition, the present invention provides a method of determining whether the stemness of stem cells is repressed, the method comprising the following steps:

(a) detecting any one or more selected from the group consisting of the phosphorylation of serine 281 in the amino acid sequence of mouse OCT4 or serine 288 in the amino acid sequence of human OCT4, the methylation of arginine 179 in the amino acid sequence of mouse OCT4, arginine 186 in the amino acid sequence of human OCT4, lysine 215 in the amino acid sequence of mouse OCT4, or lysine 222 in the amino acid sequence of human OCT4, and the phosphorylation of serine 351 in the amino acid sequence of mouse OCT4 or serine 359 in the amino acid sequence of human OCT4 from cells expressing mouse OCT4 or human OCT4; and (b) determining that the stemness of stem cells is inhibited when serine 281 in the amino acid sequence of mouse OCT4 or serine 288 in the amino acid sequence of human OCT4 is phosphorylated, when the methylation of arginine 179 in the amino acid sequence of mouse OCT4, arginine 186 in the amino acid sequence of human OCT4, lysine 215 in the amino acid sequence of mouse OCT4, or lysine 222 in the amino acid sequence of human OCT4 is inhibited, or when the phosphorylation of serine 351 in the amino acid sequence of mouse OCT4 or serine 359 in the amino acid sequence of human OCT4 is inhibited.

In the present invention, the determining method may comprise:

confirming whether Wnt signaling is activated in cells expressing mouse OCT4 or human OCT4 as the step (a); and determining that the stemness of stem cells is repressed when the Wnt signaling is not activated as the step (b).

In addition, the present invention provides a method of diagnosing whether the stemness of stem cells is repressed, the method comprising the following steps:

(a) confirming whether Wnt signaling is activated in cells expressing mouse OCT4 or human OCT4; and (b) determining that the stemness of stem cells is repressed when the Wnt signaling is not activated in the step (a).

MODE FOR THE INVENTION

EXAMPLES

Hereinafter, to help in understanding the present invention, exemplary examples will be suggested. However, the following examples are merely provided to more easily understand the present invention, and not to limit the present invention.

Example 1. Confirmation of Relationship Between Phosphorylation of Serine 281 of Mouse OCT4 and OCT4 Activation The relationship between OCT4 phosphorylation and OCT4 activation may be confirmed by a method of evaluating maintenance of embryonic stem cells. To perform the evaluation, first, a phosphorylation-inhibited mutant S281A in which serine 281 is replaced with alanine in OCT4 and a phosphorylation-mimetic mutant S281E in which serine 281 is replaced with glutamic acid in OCT4 were produced through site-directed mutagenesis. Afterward, OCT4 in the embryonic stem cells was removed, and then new cell lines expressing normal OCT4 or OCT4 mutants were produced. For cell production, a retrovirus vector expressing wild type OCT4 and a puromycin-resistant gene, or OCT4 substituted with OCT4 phosphorylation-inhibited/mimetic S281A/S281E and a puromycin-resistant gene was produced using a pMSCV-FLAG-puro vector, and then introduced, for transfection, into a mouse embryonic stem cell line ZHBTc4, which can inhibit the expression of endogenous OCT4 by treatment with doxycycline. And then, a medium was treated with puromycin to isolate a normally transfected cell line, and the isolated cell line was treated with doxycycline to inhibit the expression of endogenous OCT4 and to allow the substituted exogenous OCT4 protein to be expressed. Afterward, to confirm whether the cells were transfected with the same retrovirus, a mouse fibroblast cell line NIH3T3 in which OCT4 was not expressed was also transfected. The protein expression was confirmed through western blotting with OCT4 antibody (Santa Cruz), and as a control, ACTB antibody (Abcam) was used.

As a result, as shown in FIG. 1, it was demonstrated that OCT4 substituted with phosphorylation-inhibited/mimetic S281A/S281E was expressed at a similar level to the wild type (WT) in the NIH3T3 cell line.

In addition, before treatment with doxycycline, the cell line was washed with phosphate buffered saline (PBS), cell clusters were dissociated into single cells using trypsin-EDTA (TE) and then a cell culture medium was added so that the cell lysate had a final volume of 1 mL. Afterward, the cell lysate was dispensed into a 6-well plate at 100 μL, that is, 1/10 of the total volume of the cell lysate, treated with doxycycline and puromycin, and cultured at 37° C. in 5% $CO_2$ for 5 to 7 days. The cultured cells were stained using an alkaline phosphatase assay kit (Medsource Ozone Biomedicals), and observed using a microscope.

Figure 2:
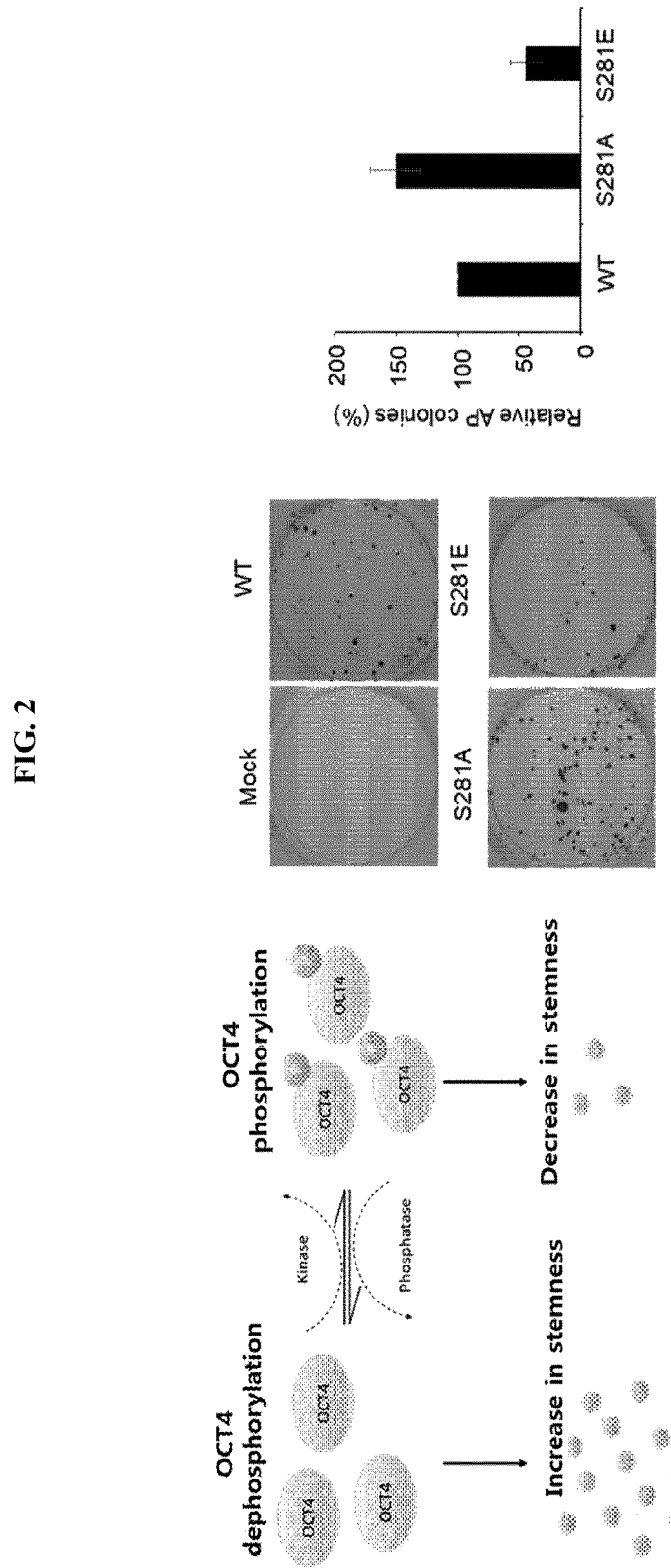
FIG. 2 shows a result of confirming the effects of inhibition of phosphorylation and mimetic mutation of serine 281 of OCT4 on the self-renewal ability of stem cells in a transformed cell line according to an exemplary embodiment of the present invention with the formation of embryonic stem cell clusters using alkaline phosphatase staining.

As a result, as shown in FIG. 2, it was demonstrated that the OCT4 phosphorylation-inhibited mutant cell line (S281A) shows an increase in the number of embryonic stem cells forming clusters, compared with the wild-type cell line as the control, whereas the OCT4 phosphorylation-mimetic mutant cell line (S281E) shows a decrease in the number of clusters, compared with the wild-type cell line.

Therefore, this result showed that, when serine 281 of mouse OCT4 (serine 288 of human OCT4) was phosphorylated, the stemness of the stem cells was repressed.

Example 2. Confirmation of Relationship Between Methylation of OCT4 Protein and OCT4 Activation 2-1. Identification of OCT4 Methylation in Mouse Embryonic Stem Cells To confirm a new methylation site of OCT4, following the isolation and purification of OCT4 protein in mouse embryonic stem cells, analysis was carried out using a mass spectrometer.

Figure 3:
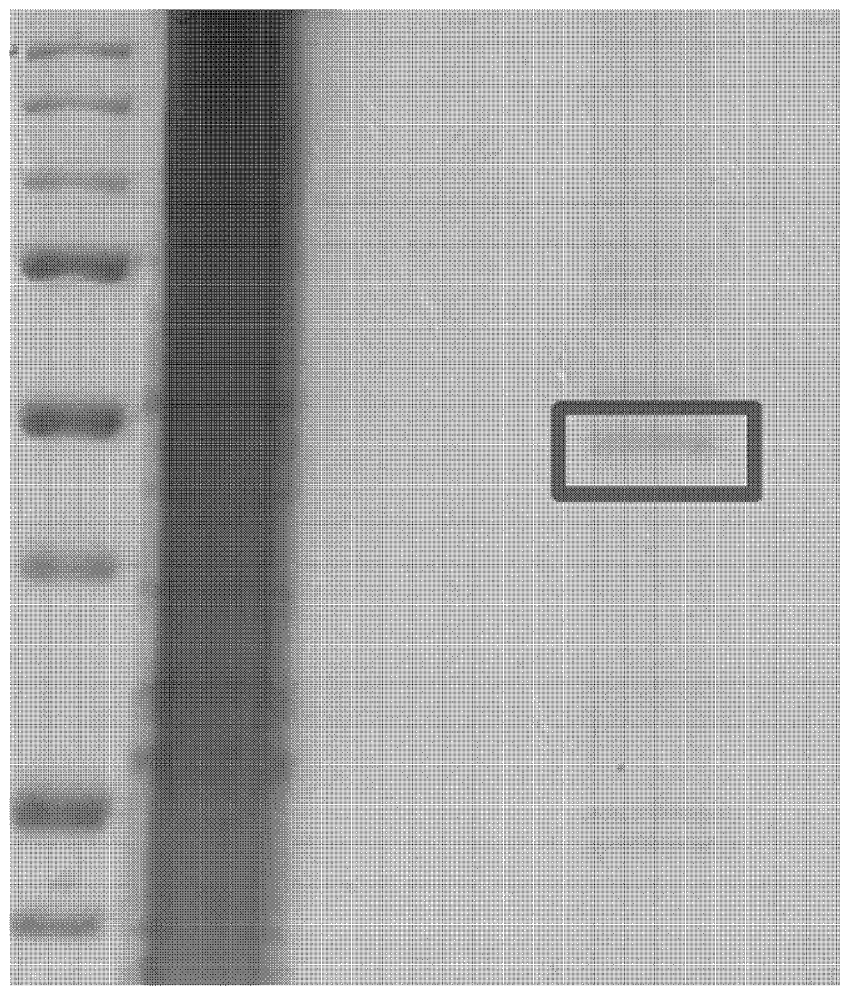
FIG. 3 shows an SDS-PAGE result of confirming FLAG-OCT4 isolated from transformed embryonic stem cells expressing FLAG-OCT4 according to an exemplary embodiment of the present invention by immunoprecipitation using an anti-FLAG antibody.

First, to identify the OCT4 protein, a mouse embryonic stem cell line in which the FLAG fusion OCT4 protein, instead of endogenous OCT4, is expressed at the same level as endogenous OCT4 was produced. Then, in the cell line, only the OCT4 protein was identified using an anti-FLAG protein antibody through immunoprecipitation, and the result is shown in FIG. 3.

Figure 4:
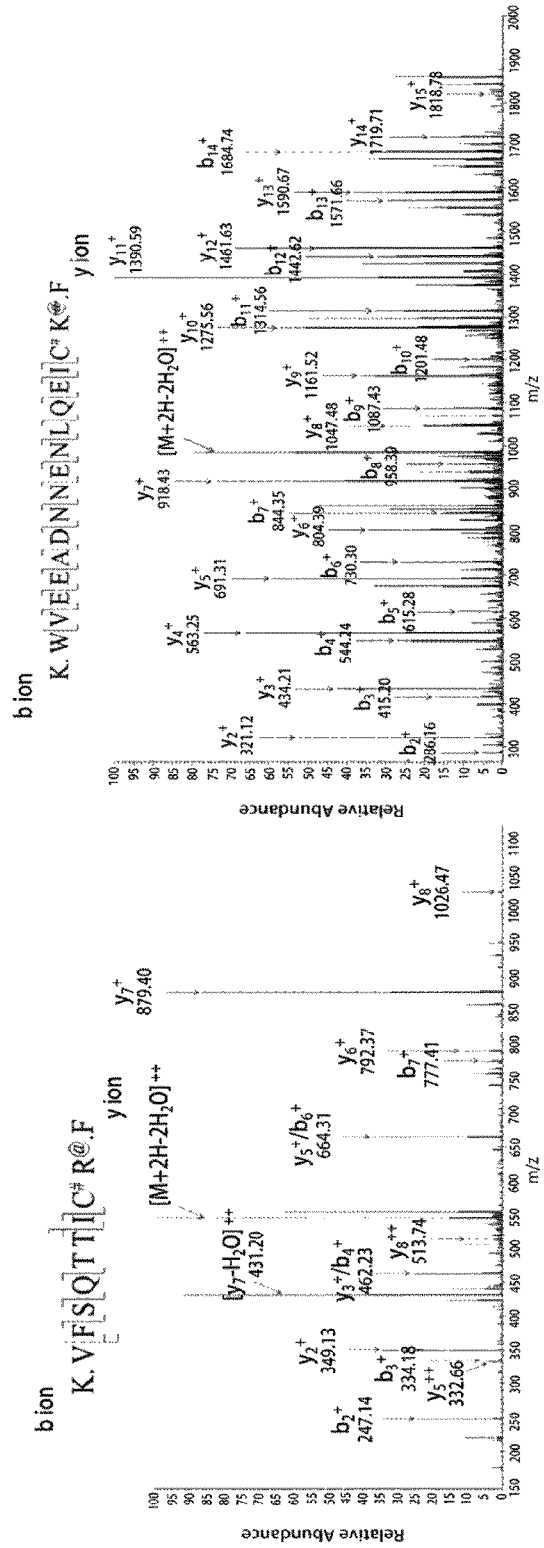
FIG. 4 shows a result of confirming an isolated FLAG-OCT4 protein according to an exemplary embodiment of the present invention using a mass spectrometer.

Afterward, the analysis with a mass spectrometer showed that, as shown in FIG. 4, new methylation occurs at the arginine 179 site of mouse OCT4 (the arginine 186 site of human OCT4) and the lysine 215 site of mouse OCT4 (the lysine 222 site of human OCT4), which were previously unknown.

2-2. Confirmation of Relationship Between OCT4 Methylation and OCT4 Activation

Figure 5:
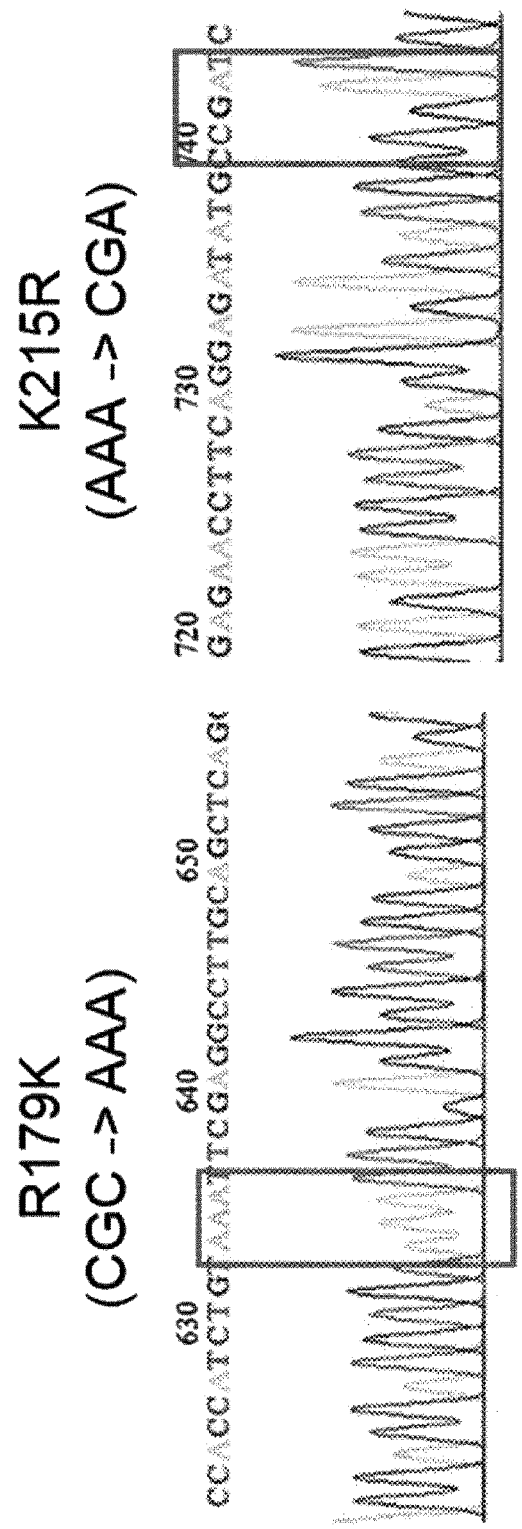
FIG. 5 shows a result of confirming the base sequence of a vector mutated so that it is impossible to methylate methylation sites (arginine 179 and lysine 215) of mouse OCT4 according to an exemplary embodiment of the present invention.

The relationship between OCT4 methylation and OCT4 activation can be confirmed by a method of evaluating maintenance of embryonic stem cells. For evaluation, first, as shown in FIG. 5, methylation-inhibited mutants R179K and K215R in which arginine 179 of OCT4 was replaced with lysine or lysine 215 of OCT4 was replaced with arginine were produced through site-directed mutagenesis. Afterward, OCT4 in embryonic stem cells was removed, and new cell lines expressing normal OCT4 or mutants were produced. For cell production, a retrovirus vector expressing wild-type OCT4 and a puromycin-resistant gene, or OCT4 substituted with OCT4 methylation-inhibited R179A/K215A and a puromycin-resistant gene was produced using a pMSCV-FLAG-puro vector, and then introduced, for transfection, into a mouse embryonic stem cell line ZHBTc4, which can inhibit the expression of endogenous OCT4 by treatment with doxycycline. And then, a medium was treated with puromycin to isolate a normally transfected cell line, and the isolated cell line was treated with doxycycline to inhibit the expression of endogenous OCT4 and to allow the substituted exogenous OCT4 protein to be expressed. Afterward, to confirm whether the cells were transfected with the same amount of retroviruses, a mouse fibroblast cell line NIH3T3 in which OCT4 was not expressed was also transfected. The protein expression was confirmed using OCT4 antibody (Santa Cruz) through western blotting, and as a control, ACTB antibody (Abcam) was used.

Figure 6:
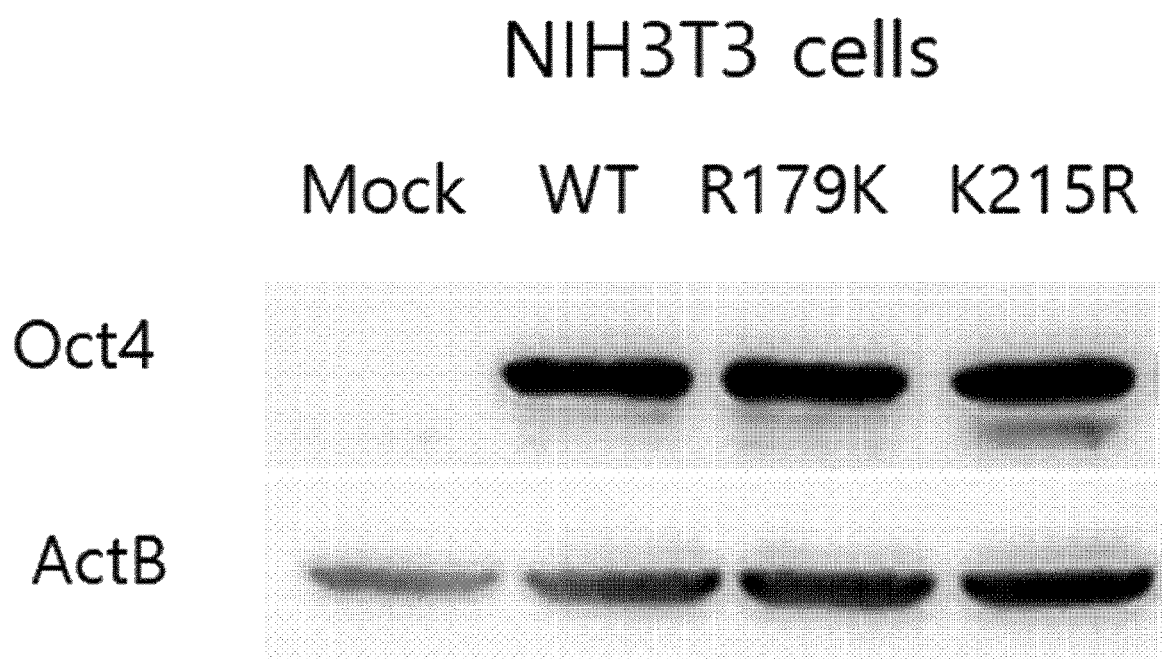
FIG. 6 shows a result of confirming that mutant OCT4 is expressed in a transformed cell line according to an exemplary embodiment of the present invention at an amount similar to the wild type (WT).

As a result, as shown in FIG. 6, it was demonstrated that OCT4 substituted with methylation-inhibited R179A/K215A was expressed at a similar level to the wild type (WT) in the NIH3T3 cell line.

In addition, before treatment with doxycycline, the cell line was washed with PBS, cell clusters were dissociated into single cells using trypsin-EDTA (TE) and then a cell culture medium was added so that the cell lysate had a final volume of 1 mL. Afterward, the cell lysate was dispensed into a 6-well plate at 100 μL, that is, ⅒ of the total volume of the cell lysate, treated with doxycycline and puromycin, and cultured at 37° C. in 5% $CO_2$ for 5 to 7 days. The cultured cells were stained using an alkaline phosphatase assay kit (Medsource Ozone Biomedicals), and observed using a microscope.

As a result, as shown in FIG. 7, it was demonstrated that the OCT4 methylation-inhibited mutant cell line shows a decrease in the number of embryonic stem cells forming clusters, compared with the wild-type cell line as the control.

Therefore, this result showed that, when the methylation of arginine 179 of mouse OCT4 (arginine 186 of human OCT4) or lysine 215 of mouse OCT4 (lysine 222 of human OCT4) is inhibited, the stemness of the stem cells is inhibited.

Example 3. Confirmation of Relationship Between Phosphorylation of Serine 351 of Mouse OCT4 and OCT4 Activation 3-1. Construction of OCT4-Phosphorylated Antibody To produce an antibody which can specifically recognize only OCT4 phosphorylation, an OCT4 protein sequence was provided from the National Center for Biotechnology Information (NCBI), the sequence of 14 amino acids with OCT4 phosphorylation was screened as shown in FIG. 8, and then antibody production was referred to an antibody production company (GenScript Biotech Corp., New Jersey, United States).

Subsequently, to confirm the produced antibody, the embryonic stem cell line was washed with PBS, the cells were lysed with a lysis buffer (20 mM Tris-Cl (pH 7.4), 150 mM NaCl, 1 mM EDTA, 1% (v/v) Triton X-100 and Protease inhibitor (#78415, Thermo Scientific)), and then identified by SDS-PAGE and western blotting using the produced antibody, OCT4 antibody (#sc-5279, Santa Cruz) and ACTB antibody (#ab8227, Abcam).

Figure 9:
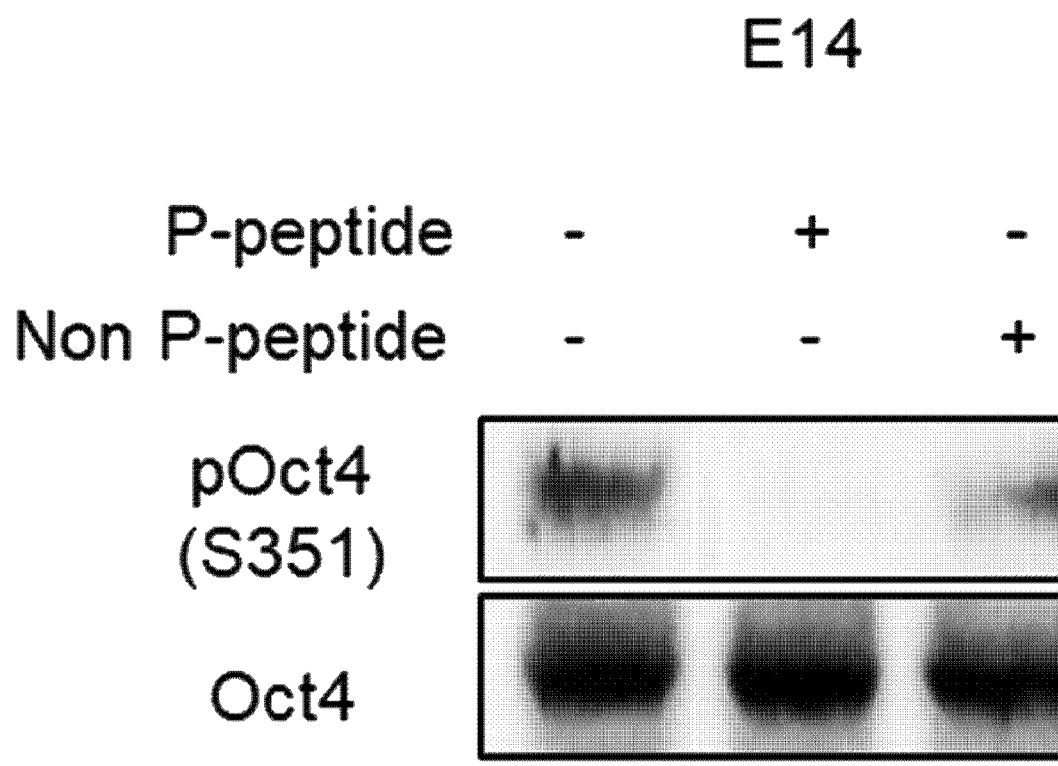
FIG. 9 shows a result of verifying an OCT4 phosphorylated antibody according to an exemplary embodiment of the present invention by recognizing a peptide at a corresponding phosphorylated site with an antibody during western blotting.

To confirm whether the OCT4 phosphorylation at the serine 351 site is specifically recognized, it was confirmed whether the recognition is inhibited when the produced antibody is recognized along with a peptide having a phosphorylated site during western blotting for a protein of the embryonic stem cell line. As a result, as shown in FIG. 9, it was demonstrated that, when the peptide having the phosphorylated site was recognized by the antibody, the phosphorylation of serine 351 of OCT4 was not recognized, and when the antibody was not recognized along with the peptide or recognized along with a peptide having a site rather than the phosphorylated site, phosphorylation was recognized.

Figure 10:
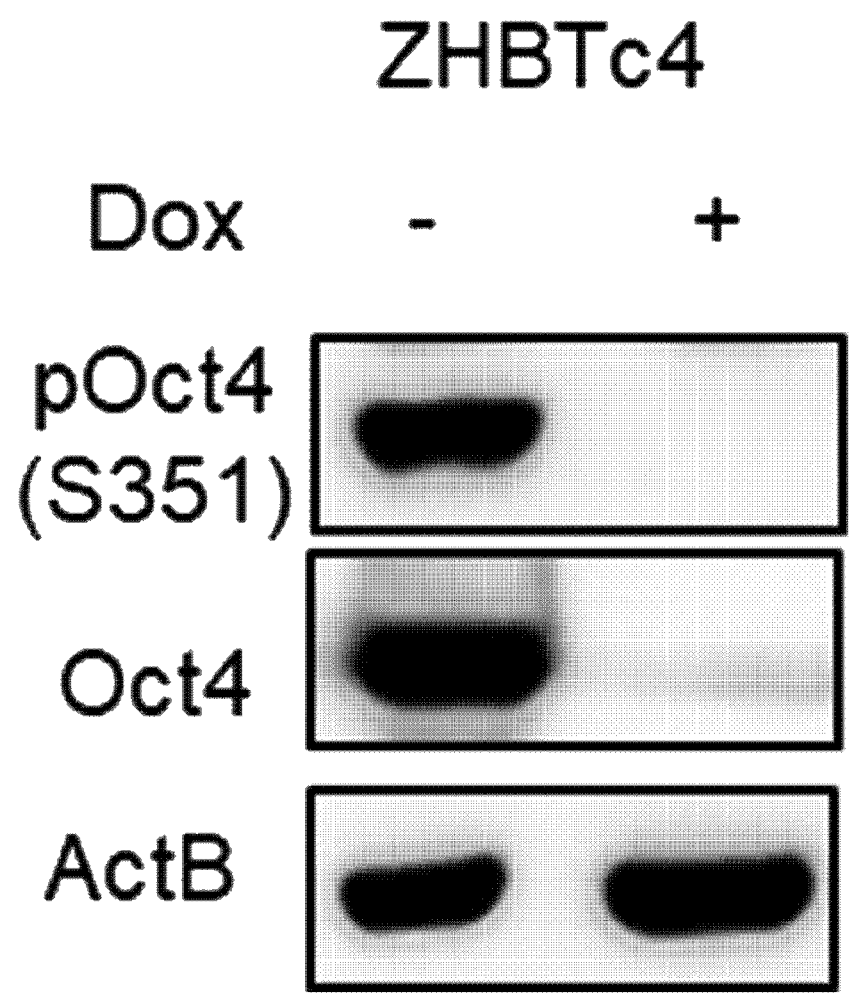
FIG. 10 shows a result of verifying whether OCT4 phosphorylation is recognized when resistant OCT4 expression is inhibited by treating an embryonic stem cell line according to an exemplary embodiment of the present invention with doxycycline.

In addition, as a result of confirming whether OCT4 or OCT4 phosphorylation was recognized depending on the presence or absence of doxycycline in the embryonic stem cell line which was treated with doxycycline to artificially inhibit the expression of endogenous OCT4, as shown in FIG. 10, it was confirmed that, when doxycycline was treated, OCT4 phosphorylation was not recognized, and when doxycycline was not treated, OCT4 phosphorylation was recognized.

Figure 11:
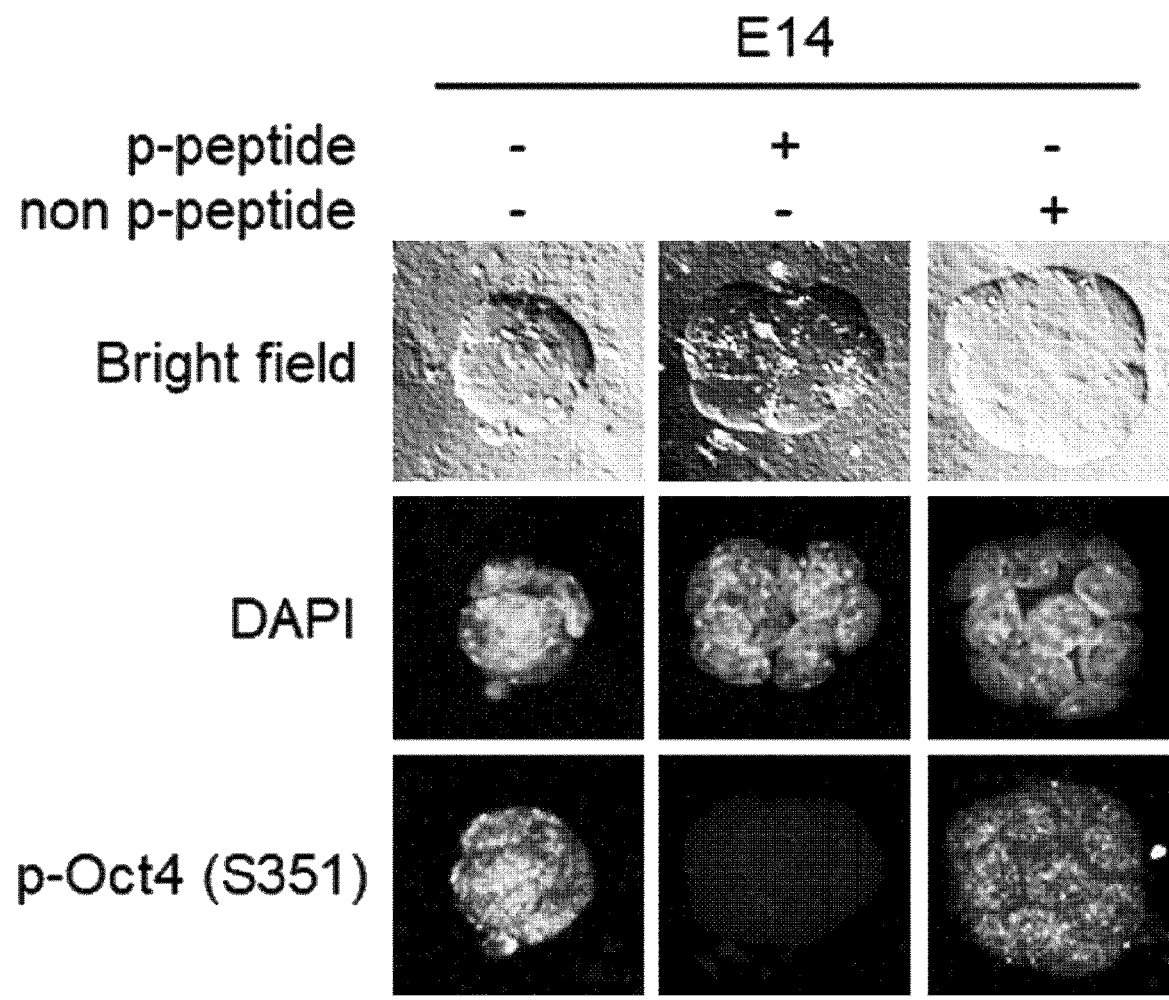
FIG. 11 shows a result of verifying a phosphorylated antibody in an embryonic stem cell line according to an exemplary embodiment of the present invention using immunofluorescence.

In addition, it was confirmed whether OCT4 phosphorylation was recognized by the antibody produced as described above through immunofluorescence. To this end, an embryonic stem cell line was washed with PBS, the cells were fixed with 4% formaldehyde (#F1635, Sigma), washed again with PBS, and treated with 0.5% Triton X-100 (#069, Amresco) to increase permeability of a cell membrane. Moreover, the reaction was blocked with 1% bovine serum albumin (BSA, #A0100-050, GeneDEPOT), and then a peptide having a phosphorylated site and a peptide having a site other than the phosphorylated site were reacted with an OCT4-phosphorylated antibody at room temperature for 2 hours. Afterward, a non-binding antibody was removed with PBS, a fluorescence-binding secondary antibody (IgG-FITC, #31569, Thermo Fisher Scientific) was treated to allow a reaction at room temperature for 1 hour, a non-binding antibody was removed again with PBS, and a nucleus was stained with 4',6-diamidino-2-phenylindole (DAPI, #CAS 28718-90-3, Calbiochem). In addition, a mounting solution was added to the cells, and protein expression was confirmed using a confocal microscope. As a result, as shown in FIG. 11, it was demonstrated that when the peptide having the phosphorylated site was recognized along with the antibody, the OCT4 phosphorylation at serine 351 was not recognized, and when a peptide having a site other than the phosphorylated site was also recognized, phosphorylation was recognized.

Figure 12:
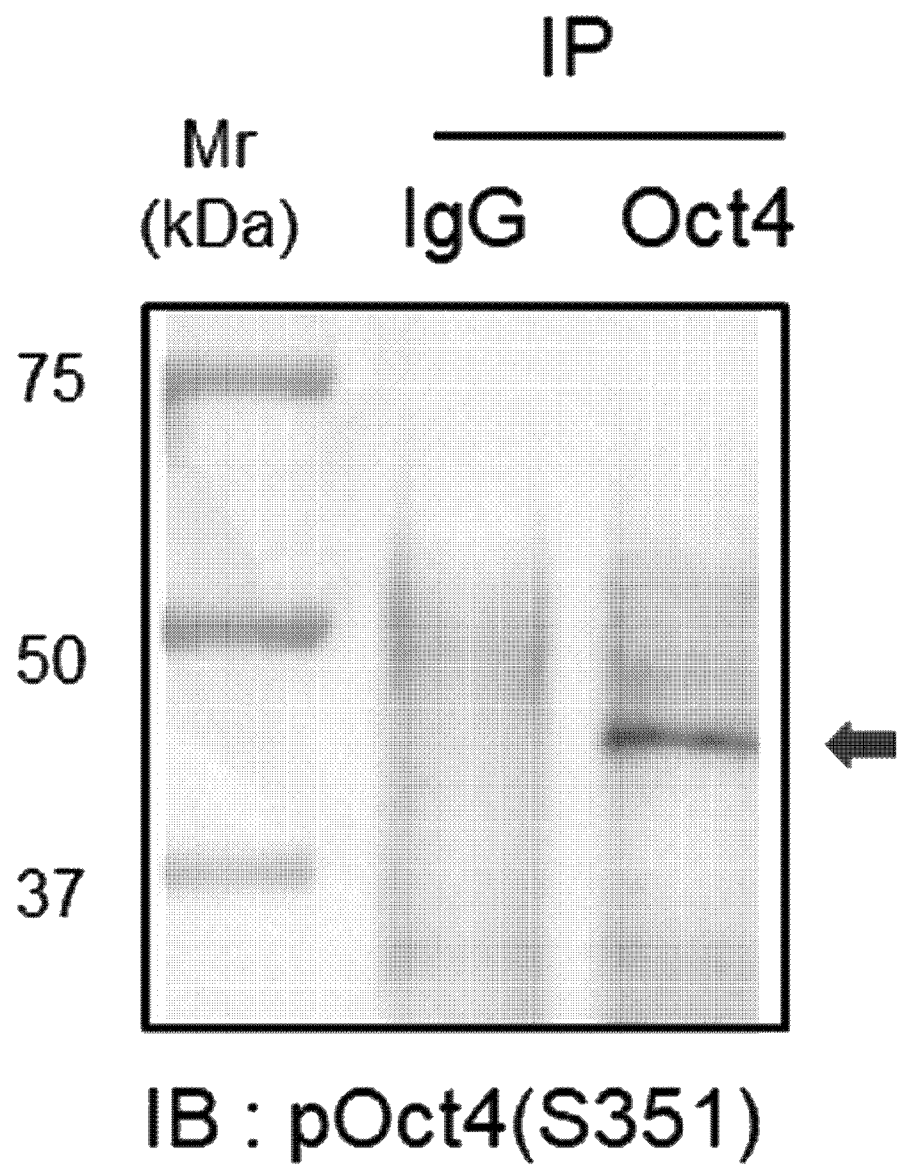
FIG. 12 shows a result of verifying a phosphorylated OCT4 antibody according to an exemplary embodiment of the present invention through immunoprecipitation.

In addition, to confirm whether the recognized OCT4 phosphorylation was derived from OCT4 protein, immunoprecipitation was performed. First, the OCT4 protein was precipitated using OCT4 antibody in the cell lysate of the embryonic stem cell line, and the result was confirmed by western blotting with an OCT4-phosphorylated antibody. Consequently, as shown in FIG. 12, it was confirmed that the recognized OCT4 phosphorylation was derived from the OCT4 protein.

3-2. Confirmation of OCT4 Phosphorylation in Human Cancer Cells

Figure 13:
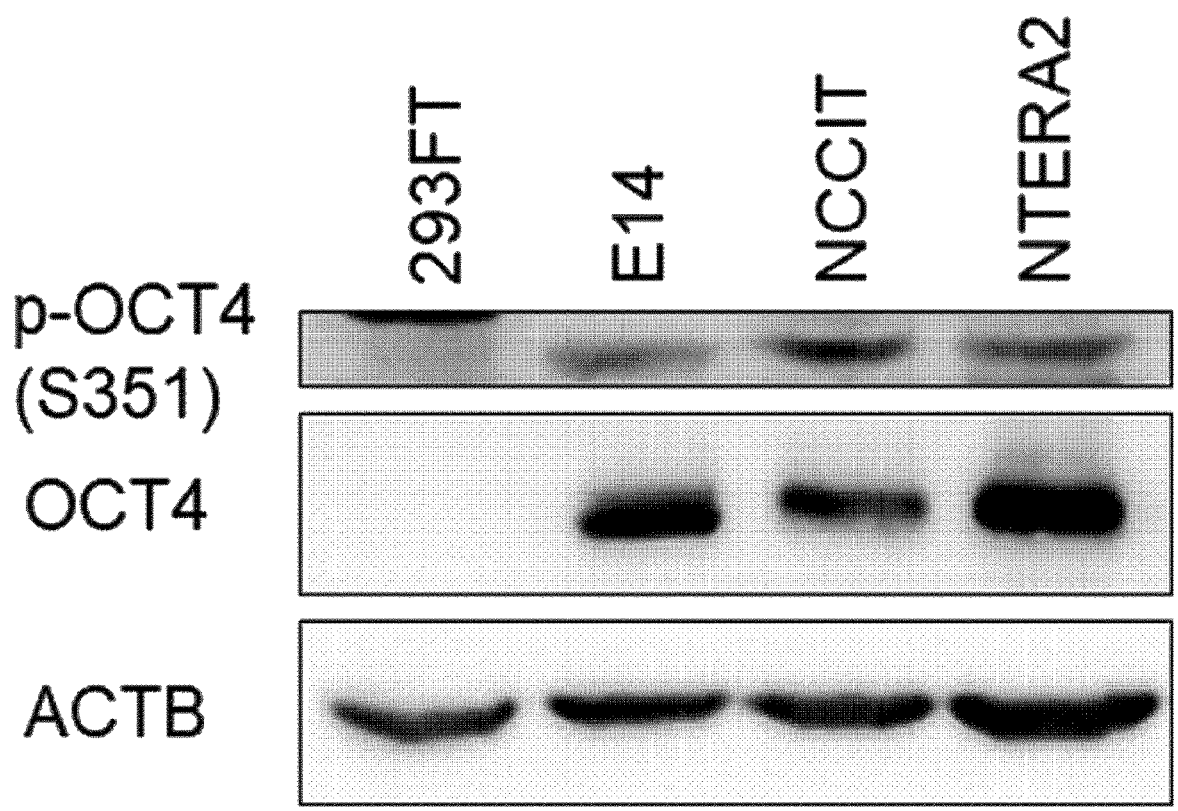
FIG. 13 shows a result of confirming whether OCT4 phosphorylation is recognized in human cancer cells according to an exemplary embodiment of the present invention.

It was confirmed whether the phosphorylation of serine 351 of OCT4 recognized in Example 3-1 was detected in human cancer cells as well as the embryonic stem cell line. To this end, NCCIT and NTERA2 cell lines having characteristics of the embryonic stem cells among human cancer cells were used, mouse embryonic stem cells (E14), as a positive control, and human fetal kidney stem cells (293FT), as a negative control, were used. Through western blotting described in Example 3-1, as shown in FIG. 13, it was observed that OCT4 phosphorylation was detected in human cancer cells.

3-3. Confirmation of Relationship Between OCT4 Phosphorylation and OCT4 Activation The relationship between OCT4 phosphorylation and OCT4 activation can be determined by a method of evaluating maintenance of the embryonic stem cells. To this end, first, a phosphorylation-inhibited mutant S351A in which serine 351 of OCT4 was replaced with alanine and a phosphorylation-mimetic mutant S351E in which serine 351 of OCT4 was replaced with glutamic acid were produced through site-directed mutagenesis. Afterward, OCT4 in the embryonic stem cells was removed, and new cell lines exhibiting normal OCT4 or OCT4 mutants were produced. For cell production, a retrovirus vector expressing wild-type OCT4 and a puromycin-resistant gene, or OCT4 substituted with OCT4 phosphorylation-inhibited/mimetic S351A/S351E and a puromycin-resistant gene was produced using a pMSCV-FLAG-puro vector, and then introduced, for transfection, into a mouse embryonic stem cell line ZHBTc4, which can inhibit the expression of endogenous OCT4 by treatment with doxycycline. And then, a medium was treated with puromycin to isolate a normally transfected cell line, and the isolated cell line was treated with doxycycline to inhibit the expression of endogenous OCT4 and to allow the substituted exogenous OCT4 protein to be expressed. To confirm whether the cells were transfected with the same amount of retroviruses, a mouse fibroblast cell line NIH3T3 in which OCT4 was not expressed was also transfected. Protein expression was confirmed through western blotting using OCT4 antibody (#sc-5279, Santa Cruz), and as a control, ACTB antibody (#ab8227, Abcam) was used.

Figure 14:
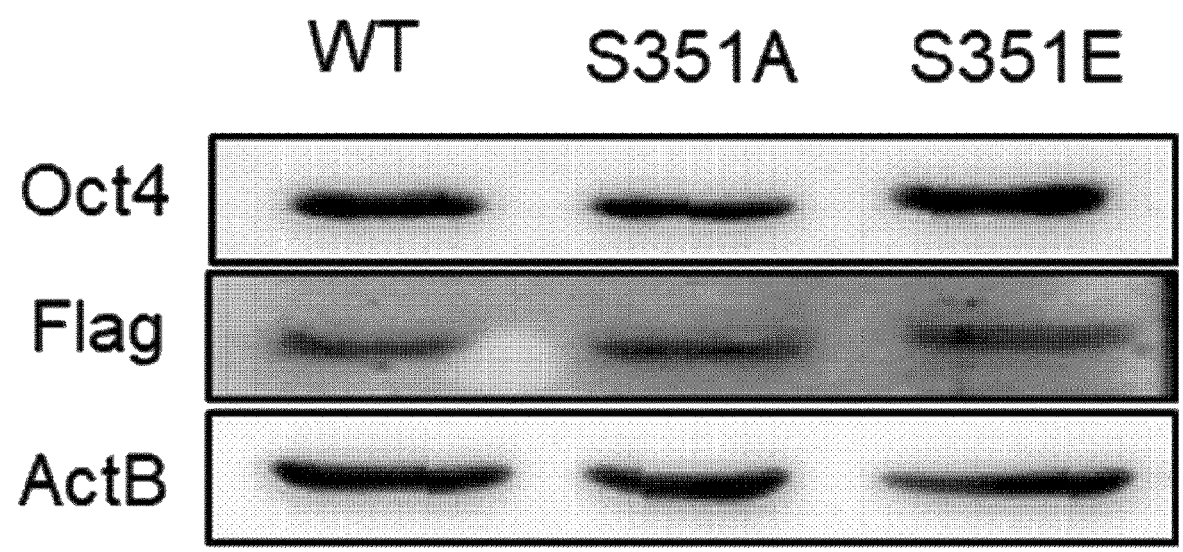
FIG. 14 shows a result of confirming that mutant OCT4 is expressed in a transformed cell line according to an exemplary embodiment of the present invention at a quantity similar to the wild type (WT).

As a result, as shown in FIG. 14, it was demonstrated that OCT4 substituted with phosphorylation-inhibited/mimetic S351A/S351E was expressed at a similar level to the wild type (WT) in the NIH3T3 cell line.

In addition, before treatment with doxycycline, the cell line was washed with PBS, cell clusters were dissociated into single cells using trypsin-EDTA (TE; Ser. No. 15/400, 054, Thermo Fisher) and then a cell culture medium was added so that the cell lysate had a final volume of 1 mL. Afterward, the cell lysate was dispensed into a 6-well plate at 100 µL, that is, 1/10 of the total volume of the cell lysate, treated with doxycycline and puromycin, and cultured at 37° C. in 5% $CO_2$ for 5 to 7 days. The cultured cells were stained using an alkaline phosphatase assay kit (Medsource Ozone Biomedicals), and observed using a microscope.

As a result, as shown in FIG. 15, it was demonstrated that the number of embryonic stem cells forming clusters in the OCT4 phosphorylation-inhibited mutant cell line (S351A), compared with the wild-type cell line as a control was decreased, whereas the number of clusters was restored in the OCT4 phosphorylation-mimetic mutant cell line (S351E) to as much as in the wild-type cell line.

In addition, a cell line stably expressing an OCT4 mutant protein was produced, and an effect of the OCT4 phosphorylation on the embryonic stem cells was confirmed. To this end, a recombinant plasmid expressing wild type OCT4 and a puromycin-resistant gene, or OCT4 substituted with OCT4 phosphorylation-inhibited/mimetic S351A/S351E and a puromycin-resistant gene was produced using a pCAG-Flag vector, and introduced, for transfection, into a mouse embryonic stem cell line ZHBTc4 inhibiting the expression of endogenous OCT4 by treatment with doxycycline using Lipofectamine 3000 (Thermo Fisher). Afterward, the medium was treated with puromycin to normally isolate the transfected cell line, the isolated cell line was treated with doxycycline to inhibit the expression of endogenous OCT4, and then exogenous OCT4 protein-substituted cell lines (ZHBTc4 OCT4-WT, ZHBTc4 OCT4-S351A and ZHBTc4 OCT4-S351E) were produced. The produced cell lines were identified by western blotting. The cell lines cultured for 4 to 8 days after treatment with doxycycline were washed with PBS, the cells were lysed with a lysis buffer (20 mM Tris-Cl (pH 7.4), 150 mM NaCl, 1 mM EDTA, 1% (v/v) Triton X-100 and protease inhibitors), and then subjected to SDS-PAGE and western blotting using an OCT4 antibody and a FLAG antibody (#F3165, Sigma). As a control, an ACTB antibody was used.

As a result, as shown in FIG. 16, it was demonstrated that wild-type OCT4 or S351A/5351E-substituted OCT4 was normally transformed, and the exogenous OCT4 protein was doxycycline-dependently expressed as much as the endogenous OCT4 protein.

In addition, the produced cell line was divided into single cells, and 1000 single cells were dispensed into each well of a 6-well plate and then cultured at 37° C., in 5% $CO_2$ for 5 to 7 days while treating doxycycline and puromycin. The cultured cells were stained using an alkaline phosphatase assay kit (Medsource Ozone Biomedicals), and observed using a microscope.

As a result, as shown in FIG. 17, it was demonstrated that the cells stably expressing phosphorylation-inhibited OCT4 (S351A), compared with the wild type as a control, had widely spread cell morphology, whereas the cells expressing phosphorylation-mimetic OCT4 (S351E) had a dome-shaped cell morphology like the control.

In addition, the self-renewal ability of stem cells was evaluated using a SSEA-1 antibody as a marker for self-renewal ability of a stem cell. To this end, 1000 single cells were dispensed into each well of a 6-well plate, cultured at 37° C. in 5% $CO_2$ for 5 to 7 days while treating doxycycline and puromycin, stained with SSEA-1 and identified by fluorescence activated cell sorting (FACS).

As a result, as shown in FIG. 18, the cell line expressing phosphorylation-mimetic OCT4 (S351E), that is, ZHBTc4 OCT4-S351E, was stained with SSEA-1 like the wild type (ZHBTc4 OCT4-WT), whereas the cell line expressing phosphorylation-inhibited OCT4 (S351A), that is, ZHBTc4 OCT4-S351A, was less stained.

Example 4. Confirmation of Relationship Between OCT4 Phosphorylation and Regulation of Wnt Signaling 4-1. Evaluation of Effect of OCT4 Phosphorylation on Embryonic Stem Cells The embryonic stem cell lines (ZHBTc4 OCT4-WT and ZHBTc4 OCT4-S351A) stably expressing exogenous OCT4, which were produced by the method described in Example 3-3 were treated with doxycycline, total RNA was purified from the cultured cells using a RNeasy Purification Kit (#74104, Qiagen) and then subjected to total RNA-sequencing, conducted by Macrogen (Korea). Through the total RNA-sequencing, a gene for directly regulating OCT4 using known ChIP data was screened. The result is shown in FIG. 19.

A pathway analysis for the gene screened thereby was carried out, and the result was visualized using a visualization program (Cytoscape, 3.6.1). According to the pathway analysis, as shown in FIG. 20, it was confirmed that there were changes in a pathway related to the pluripotency of stem cells and a Wnt signaling pathway. Particularly, it was confirmed that, in the Wnt signaling pathway, when phosphorylation-inhibited mutant OCT4 was expressed, Wnt signaling was inhibited through Gene Set Enrichment Analysis (GSEA), and the result is shown in FIG. 21.

4-2. Confirmation of Relationship Between OCT4 Phosphorylation and Wnt Signaling The produced cell line produced by the same method as described in Example 3-3 was divided into single cells, and 1000 single cells were dispensed into each well of a 6-well plate and then cultured at 37° C., in 5% $CO_2$ for 5 to 7 days while treating doxycycline, puromycin, and recombinant protein WNT3A or compound CHIR9901, which can artificially activate Wnt signaling. The cultured cells were stained using an alkaline phosphatase assay kit, and observed using a microscope.

Figure 22:
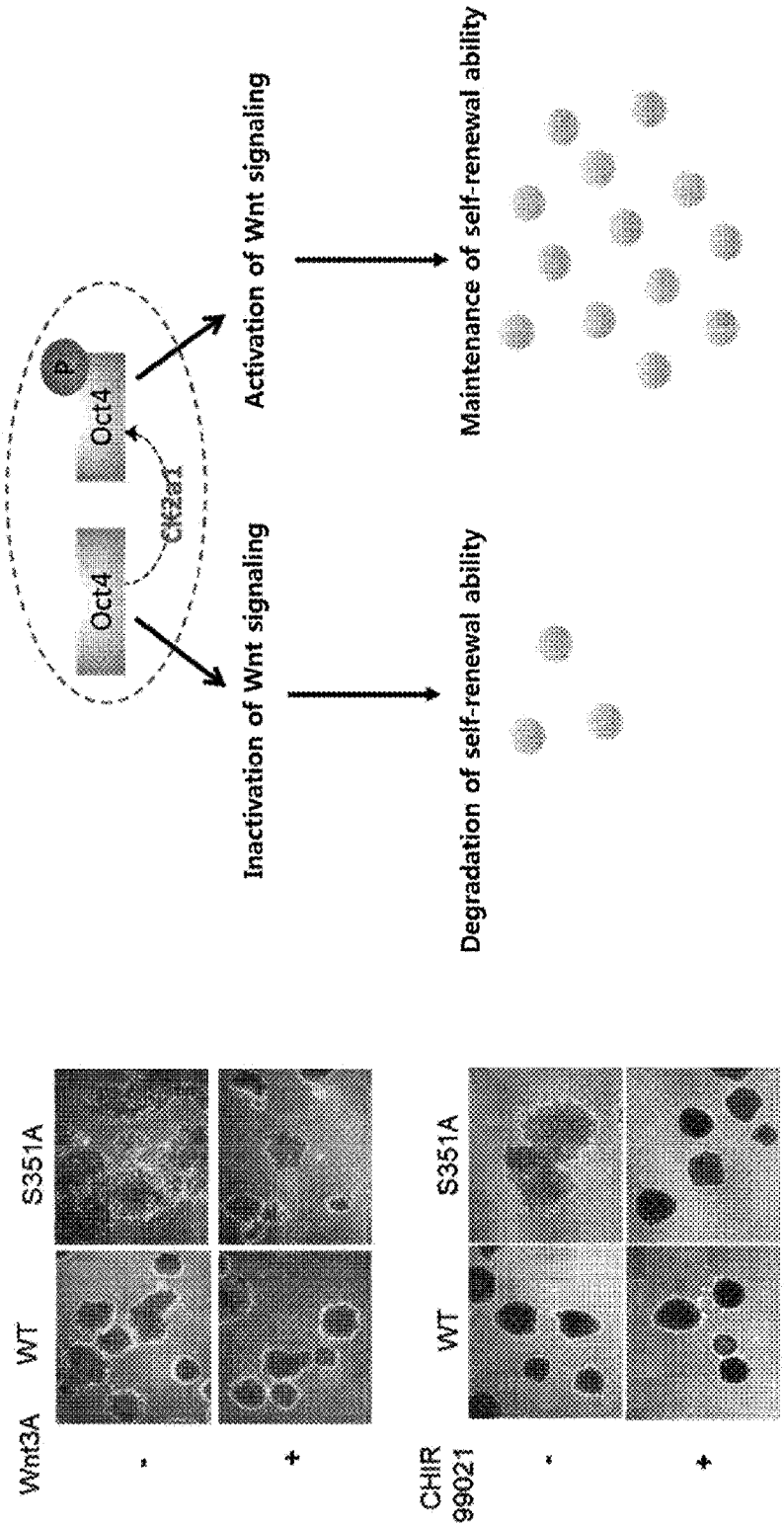
FIG. 22 shows a result of confirming the self-renewal ability of stem cells when Wnt signaling is artificially activated in a transduced embryonic stem cell line according to an exemplary embodiment of the present invention using alkaline phosphatase staining.

As a result, as shown in FIG. 22, it was demonstrated that, when Wnt signaling was artificially activated in the cells stably expressing phosphorylation-inhibited OCT4, the self-renewal ability of stem cells was restored.

In addition, the self-renewal ability of stem cells was evaluated using a self-renewal ability of stem cells, that is, SSEA-1 antibody, and therefore, as shown in FIG. 23, it was confirmed that, when the Wnt signaling was activated, the self-renewal ability was restored.

Example 5. Confirmation of OCT4 Phosphorylation-Inducing Kinase

To confirm the relationship between CSNK2A1 and OCT4 phosphorylation using a kinase inducing the phosphorylation of serine 351 of OCT4, a cell line for regulating the inhibition of CSNK2A1 expression was produced. To this end, a lentivirus doxycycline-dependently expressing shRNA of SEQ ID NO: 5 or 6 was produced and transfected into an embryonic stem cell line E14, thereby producing a cell line capable of regulating CSNK2A1 expression using doxycycline. Afterward, following western blotting performed by the same method as described in Example 3-1, as shown in FIG. 24, it was confirmed that a kinase inducing OCT4 phosphorylation is CSNK2A1.

In addition, an in vitro kinase assay was performed using a GST fusion recombinant OCT4 protein and GST fusion recombinant CSNK2A1. 1 µg of the GST fusion OCT4 recombinant protein and 0.2 µg of the GST fusion CSNK2A1 recombinant protein were mixed with 0.5 mM ATP in a kinase buffer (60 mM HEPES-NaOH pH 7.5, 3 mM $MgCl_2$, 3 mM $MnCl_2$, 3 µM Na-orthovanadate, 1.2 mM DTT) to allow a reaction at 30° C. for 30 minutes, followed by SDS-PAGE and western blotting. As a result, as shown in FIG. 25, it was demonstrated that, in the presence of OCT4 and CSNK2A1, OCT4 phosphorylation was recognized by a phosphorylated antibody.

From the above-described examples, it was confirmed that the OCT4 modification-regulating material of the present invention regulates OCT4 modification (post-translational modification), thereby regulating the self-renewal ability of stem cells, and the result is schematically shown in FIG. 26.

It would be understood by those of ordinary skill in the art that the above descriptions of the present invention are exemplary, and the exemplary embodiments disclosed herein can be easily modified into other specific forms without changing the technical spirit or essential features of the present invention. Therefore, it should be interpreted that the exemplary embodiments described above are exemplary in all aspects, and are not limitative.

INDUSTRIAL APPLICABILITY

As the OCT4 modification-regulating material according to the present invention regulates OCT4 phosphorylation or methylation and inhibits Wnt signaling, the stemness of various stem cells can be effectively degraded, and therefore the OCT4 modification-regulating material can be effectively used in inhibition of proliferation, recurrence and metastasis of cancer, and resistance to an anticancer agent.

The invention claimed is:

1. A method of inhibiting stemness of stem cells through regulation of OCT4 modification, comprising at least one selected from the group consisting of
   (a) administering a vector for transformation to a stem cell, the vector comprising genes encoding OCT4 phosphorylated at serine 281 in the amino acid sequence of mouse octamer-binding transcription factor 4 (OCT4) or serine 288 in the amino acid sequence of human OCT4;
   (b) administering a vector for transformation to a stem cell, the vector comprising genes encoding OCT4 such that the methylation of arginine 179 in the amino acid sequence of mouse OCT4, arginine 186 in the amino acid sequence of human OCT4, lysine 215 in the amino acid sequence of mouse OCT4, or lysine 222 in the amino acid sequence of human OCT4 is inhibited; and
   (c) administering a vector for transformation to a stem cell, the vector comprising genes encoding OCT4 such that the phosphorylation of serine 351 in the amino acid sequence of mouse OCT4 or serine 359 in the amino acid sequence of human OCT4 is inhibited.

2. The method according to claim 1, further comprising: in (c), blocking activation of Wnt signaling.

3. The method according to claim 1, wherein the amino acid sequence of mouse OCT4 is represented by the amino acid sequence of SEQ ID NO: 1.

4. The method according to claim 1, wherein the amino acid sequence of human OCT4 is represented by the amino acid sequence of SEQ ID NO: 2.

5. The method according to claim 1, wherein the stem cells are selected from the group consisting of embryonic stem cells, gametes, cancer stem cells, and a combination thereof.

6. A method of screening a material for repressing the stemness of stem cells, the method comprising:
   (a) treating cells expressing mouse octamer-binding transcription factor 4 (OCT4) or human OCT4 with a candidate material or a vector for transformation, wherein the vector comprises at least one selected from the group consisting of:

genes encoding OCT4 phosphorylated at serine 281 in the amino acid sequence of mouse octamer-binding transcription factor 4 (OCT4) or serine 288 in the amino acid sequence of human OCT4;

genes encoding OCT4 such that the methylation of arginine 179 in the amino acid sequence of mouse OCT4, arginine 186 in the amino acid sequence of human OCT4, lysine 215 in the amino acid sequence of mouse OCT4, or lysine 222 in the amino acid sequence of human OCT4 is inhibited; and genes encoding OCT4 such that the phosphorylation of serine 351 in the amino acid sequence of mouse OCT4 or serine 359 in the amino acid sequence of human OCT4 is inhibited;

(b) comparing at least one selected from the group consisting of the phosphorylation of serine 281 in the amino acid sequence of mouse OCT4 or serine 288 in the amino acid sequence of human OCT4, the methylation of arginine 179 in the amino acid sequence of mouse OCT4, arginine 186 in the amino acid sequence of human OCT4, lysine 215 in the amino acid sequence of mouse OCT4, or lysine 222 in the amino acid sequence of human OCT4, and the phosphorylation of serine 351 in the amino acid sequence of mouse OCT4 or serine 359 in the amino acid sequence of human OCT4 between the cells treated with the candidate material and the cells treated with the vector; and (c) selecting the candidate material as a material for repressing the stemness of stem cells when serine 281 in the amino acid sequence of mouse OCT4 or serine 288 in the amino acid sequence of human OCT4 is phosphorylated, when the methylation of arginine 179 in the amino acid sequence of mouse OCT4, arginine 186 in the amino acid sequence of human OCT4, lysine 215 in the amino acid sequence of mouse OCT4, or lysine 222 in the amino acid sequence of human OCT4 is inhibited, or when the phosphorylation of serine 351 in the amino acid sequence of mouse OCT4 or serine 359 in the amino acid sequence of human OCT4 is inhibited.

7. The method according to claim 6, comprising:
detecting whether Wnt signaling is activated in cells in (b); and
selecting the candidate material as a material for repressing the stemness of stem cells when the Wnt signaling is not activated in (c).

8. A method of diagnosing whether the stemness of stem cells is repressed, the method comprising:
(a) comparing at least one selected from the group consisting of the phosphorylation of serine 281 in the amino acid sequence of mouse octamer-binding transcription factor 4 (OCT4) or serine 288 in the amino acid sequence of human OCT4, the methylation of arginine 179 in the amino acid sequence of mouse OCT4, arginine 186 in the amino acid sequence of human OCT4, lysine 215 in the amino acid sequence of mouse OCT4, or lysine 222 in the amino acid sequence of human OCT4, and the phosphorylation of serine 351 in the amino acid sequence of mouse OCT4 or serine 359 in the amino acid sequence of human OCT4 between cells expressing mouse OCT4 or human OCT4 and cells treated with a vector comprising at least one selected from the group consisting of:

genes encoding OCT4 phosphorylated at serine 281 in the amino acid sequence of mouse octamer-binding transcription factor 4 (OCT4) or serine 288 in the amino acid sequence of human OCT4;

genes encoding OCT4 such that the methylation of arginine 179 in the amino acid sequence of mouse OCT4, arginine 186 in the amino acid sequence of human OCT4, lysine 215 in the amino acid sequence of mouse OCT4, or lysine 222 in the amino acid sequence of human OCT4 is inhibited; and genes encoding OCT4 such that the phosphorylation of serine 351 in the amino acid sequence of mouse OCT4 or serine 359 in the amino acid sequence of human OCT4 is inhibited; and (b) determining that the stemness of stem cells is repressed when serine 281 in the amino acid sequence of mouse OCT4 or serine 288 in the amino acid sequence of human OCT4 is phosphorylated, when the methylation of arginine 179 in the amino acid sequence of mouse OCT4, arginine 186 in the amino acid sequence of human OCT4, lysine 215 in the amino acid sequence of mouse OCT4, or lysine 222 in the amino acid sequence of human OCT4 is inhibited, or when the phosphorylation of serine 351 in the amino acid sequence of mouse OCT4 or serine 359 in the amino acid sequence of human OCT4 is inhibited.

9. The method according to claim 8, comprising:
confirming whether Wnt signaling is activated in cells expressing mouse OCT4 or human OCT4 in (a); and
determining that the stemness of stem cells is repressed when the Wnt signaling is not activated in (b).

* * * * *

SEQUENCE LISTING

```
<160> NUMBER OF SEQ ID NOS: 8

<210> SEQ ID NO 1
<211> LENGTH: 352
<212> TYPE: PRT
<213> ORGANISM: Mus musculus
<220> FEATURE:
<221> NAME/KEY: PEPTIDE
<222> LOCATION: (1)..(352)
<223> OTHER INFORMATION: POU domain, class 5, transcription factor 1
      isoform 1

<400> SEQUENCE: 1

Met Ala Gly His Leu Ala Ser Asp Phe Ala Phe Ser Pro Pro Pro Gly
1               5                   10                  15

Gly Gly Asp Gly Ser Ala Gly Leu Glu Pro Gly Trp Val Asp Pro Arg
                20                  25                  30

Thr Trp Leu Ser Phe Gln Gly Pro Pro Gly Gly Pro Gly Ile Gly Pro
            35                  40                  45

Gly Ser Glu Val Leu Gly Ile Ser Pro Cys Pro Pro Ala Tyr Glu Phe
        50                  55                  60

Cys Gly Gly Met Ala Tyr Cys Gly Pro Gln Val Gly Leu Gly Leu Val
65                  70                  75                  80

Pro Gln Val Gly Val Glu Thr Leu Gln Pro Glu Gly Gln Ala Gly Ala
                85                  90                  95

Arg Val Glu Ser Asn Ser Glu Gly Thr Ser Ser Glu Pro Cys Ala Asp
                100                 105                 110

Arg Pro Asn Ala Val Lys Leu Glu Lys Val Glu Pro Thr Pro Glu Glu
            115                 120                 125

Ser Gln Asp Met Lys Ala Leu Gln Lys Glu Leu Glu Gln Phe Ala Lys
```

```
                130                 135                 140
Leu Leu Lys Gln Lys Arg Ile Thr Leu Gly Tyr Thr Gln Ala Asp Val
145                 150                 155                 160

Gly Leu Thr Leu Gly Val Leu Phe Gly Lys Val Phe Ser Gln Thr Thr
                165                 170                 175

Ile Cys Arg Phe Glu Ala Leu Gln Leu Ser Leu Lys Asn Met Cys Lys
                180                 185                 190

Leu Arg Pro Leu Leu Glu Lys Trp Val Glu Glu Ala Asp Asn Asn Glu
                195                 200                 205

Asn Leu Gln Glu Ile Cys Lys Ser Glu Thr Leu Val Gln Ala Arg Lys
                210                 215                 220

Arg Lys Arg Thr Ser Ile Glu Asn Arg Val Arg Trp Ser Leu Glu Thr
225                 230                 235                 240

Met Phe Leu Lys Cys Pro Lys Pro Ser Leu Gln Gln Ile Thr His Ile
                245                 250                 255

Ala Asn Gln Leu Gly Leu Glu Lys Asp Val Val Arg Val Trp Phe Cys
                260                 265                 270

Asn Arg Arg Gln Lys Gly Lys Arg Ser Ser Ile Glu Tyr Ser Gln Arg
                275                 280                 285

Glu Glu Tyr Glu Ala Thr Gly Thr Pro Phe Pro Gly Gly Ala Val Ser
290                 295                 300

Phe Pro Leu Pro Pro Gly Pro His Phe Gly Thr Pro Gly Tyr Gly Ser
305                 310                 315                 320

Pro His Phe Thr Thr Leu Tyr Ser Val Pro Phe Pro Glu Gly Glu Ala
                325                 330                 335

Phe Pro Ser Val Pro Val Thr Ala Leu Gly Ser Pro Met His Ser Asn
                340                 345                 350

<210> SEQ ID NO 2
<211> LENGTH: 360
<212> TYPE: PRT
<213> ORGANISM: Homo sapiens
<220> FEATURE:
<221> NAME/KEY: PEPTIDE
<222> LOCATION: (1)..(360)
<223> OTHER INFORMATION: POU domain, class 5, transcription factor 1
      isoform 1

<400> SEQUENCE: 2

Met Ala Gly His Leu Ala Ser Asp Phe Ala Phe Ser Pro Pro Pro Gly
1               5                   10                  15

Gly Gly Gly Asp Gly Pro Gly Gly Pro Glu Pro Gly Trp Val Asp Pro
                20                  25                  30

Arg Thr Trp Leu Ser Phe Gln Gly Pro Pro Gly Gly Pro Gly Ile Gly
                35                  40                  45

Pro Gly Val Gly Pro Gly Ser Glu Val Trp Gly Ile Pro Pro Cys Pro
50                  55                  60

Pro Pro Tyr Glu Phe Cys Gly Gly Met Ala Tyr Cys Gly Pro Gln Val
65                  70                  75                  80

Gly Val Gly Leu Val Pro Gln Gly Gly Leu Glu Thr Ser Gln Pro Glu
                85                  90                  95

Gly Glu Ala Gly Val Gly Val Glu Ser Asn Ser Asp Gly Ala Ser Pro
                100                 105                 110

Glu Pro Cys Thr Val Thr Pro Gly Ala Val Lys Leu Glu Lys Glu Lys
                115                 120                 125

Leu Glu Gln Asn Pro Glu Glu Ser Gln Asp Ile Lys Ala Leu Gln Lys
```

```
            130                 135                 140
Glu Leu Glu Gln Phe Ala Lys Leu Leu Lys Gln Lys Arg Ile Thr Leu
145                 150                 155                 160

Gly Tyr Thr Gln Ala Asp Val Gly Leu Thr Leu Gly Val Leu Phe Gly
                165                 170                 175

Lys Val Phe Ser Gln Thr Thr Ile Cys Arg Phe Glu Ala Leu Gln Leu
            180                 185                 190

Ser Phe Lys Asn Met Cys Lys Leu Arg Pro Leu Leu Gln Lys Trp Val
        195                 200                 205

Glu Glu Ala Asp Asn Asn Glu Asn Leu Gln Glu Ile Cys Lys Ala Glu
    210                 215                 220

Thr Leu Val Gln Ala Arg Lys Arg Lys Arg Thr Ser Ile Glu Asn Arg
225                 230                 235                 240

Val Arg Gly Asn Leu Glu Asn Leu Phe Leu Gln Cys Pro Lys Pro Thr
                245                 250                 255

Leu Gln Gln Ile Ser His Ile Ala Gln Gln Leu Gly Leu Glu Lys Asp
            260                 265                 270

Val Val Arg Val Trp Phe Cys Asn Arg Arg Gln Lys Gly Lys Arg Ser
        275                 280                 285

Ser Ser Asp Tyr Ala Gln Arg Glu Asp Phe Glu Ala Ala Gly Ser Pro
    290                 295                 300

Phe Ser Gly Gly Pro Val Ser Phe Pro Leu Ala Pro Gly Pro His Phe
305                 310                 315                 320

Gly Thr Pro Gly Tyr Gly Ser Pro His Phe Thr Ala Leu Tyr Ser Ser
                325                 330                 335

Val Pro Phe Pro Glu Gly Glu Ala Phe Pro Pro Val Ser Val Thr Thr
            340                 345                 350

Leu Gly Ser Pro Met His Ser Asn
        355                 360

<210> SEQ ID NO 3
<211> LENGTH: 1353
<212> TYPE: RNA
<213> ORGANISM: Mus musculus
<220> FEATURE:
<221> NAME/KEY: gene
<222> LOCATION: (1)..(1353)
<223> OTHER INFORMATION: POU domain, class 5, transcription factor 1
      (Pou5f1), transcript variant 1, mRNA

<400> SEQUENCE: 3
gaggugaaac cgucccuagg ugagccgucu uuccaccagg ccccggcuc ggggugccca      60 ccuuccccau ggcuggacac cuggcuucag acuucgccuu cucaccccca ccaggugggg   120
gugauggguc agcagggcug gagccgggcu ggugggaucc ucgaaccugg cuaagcuucc   180
aagggccucc aggugggccu ggaaucggac caggcucaga gguauugggg aucuccccau   240
guccgcccgc auacgaguuc ugcggaggga uggcauacug uggaccucag uuggacugg   300 gccuaguccc ccaaguuggc guggagacuu ugcagccuga gggccaggca ggagcacgag   360
uggaaagcaa cucagaggga accuccucug agcccugugc cgaccgcccc aaugccguga   420
aguuggagaa ggaggaacca cucccgagg aguccccagga caugaaagcc cugcagaagg   480
agcuagaaca guuugccaag cugcugaagc agaagaggau caccuugggg uacacccagg   540
ccgacugggg gcucacccug ggcguucucu uggaaaggu guucagccag accaccaucu   600
gucgcuucga ggccuugcag cucagcccuua agaacauguc uaagcugcgg ccccugcugg   660
```

| | |
|---|---|
| agaaguggggu ggaggaagcc gacaacaaug agaaccuuca ggagauaugc aaaucggaga | 720 |
| cccuggugca ggcccggaag agaaagcgaa cuagcauuga gaaccgugug agguggaguc | 780 |
| uggagaccau guuucugaag ugcccgaagc ccucccuaca gcagaucacu cacaucgcca | 840 |
| aucagcuugg gcuagagaag gaugugguuc gaguaugguu cuguaaccgg cgccagaagg | 900 |
| gcaaaagauc aaguauugag uauucccaac gagaagagua ugaggcuaca gggacaccuu | 960 |
| ucccagggggg ggcuguaucc uuccucugc ccccaggucc ccacuuuggc ccccaggcu | 1020 |
| auggaagccc ccacuucacc acacucuacu cagucccuuu ccugagggc gaggccuuuc | 1080 |
| ccucuguucc cgucacugcu cugggcucuc ccaugcauuc aaacugaggc accagcccuc | 1140 |
| ccuggggaug cugugagcca aggcaaggga gguagacaag agaaccugga gcuuuggggu | 1200 |
| uaaauucuuu uacugaggag ggauuaaaag cacaacaggg gugggggggug ggaugggggaa | 1260 |
| agaagcucag ugaugcuguu gaucaggagc cuggccuguc ugucacucau cauuuuguuc | 1320 |
| uuaaauaaag acugggacac acaguagaua gcu | 1353 |

<210> SEQ ID NO 4
<211> LENGTH: 1430
<212> TYPE: RNA
<213> ORGANISM: Homo sapiens
<220> FEATURE:
<221> NAME/KEY: gene
<222> LOCATION: (1)..(1430)
<223> OTHER INFORMATION: POU class 5 homeobox 1 (POU5F1), transcript
      variant 1, mRNA

<400> SEQUENCE: 4

| | |
|---|---|
| agagaggggu ugaguagucc cuucgcaagc ccucauuuca ccaggccccc ggcuuggggc | 60 |
| gccuuccuuc cccauggcgg gacaccuggc uucggauuuc gccuucgc ccccuccagg | 120 |
| uggguggaggu gaugggccag gggggccgga gccgggcugg guugauccuc ggaccuggcu | 180 |
| aagcuuccaa ggcccuccug gagggccagg aaucggccg ggguuggc caggcucuga | 240 |
| ggugugggggg auucccccau gccccccgcc guaugaguuc ugugggggga uggcguacug | 300 |
| ugggccccag guuggagugg ggcuaguagcc ccaaggcggc uuggagaccu cucagccuga | 360 |
| gggcgaagca ggagucgggg uggagagcaa cuccgauggg gccucccgg agcccugcac | 420 |
| cgucaccccu ggugccguga agcuggagaa ggagaagcug gagcaaaacc cggaggaguc | 480 |
| ccaggacauc aaagcucugc agaaagaacu cgagcaauuu gccaagcucc ugaagcagaa | 540 |
| gaggaucacc cugggauaua cacaggccga gugggcuc acccggggggg uucuauuugg | 600 |
| gaagguauuc agccaaacga ccaucugccg cuuugaggcu cugcagccuua gcuucaagaa | 660 |
| caugguguaag cugcggcccu ugcugcagaa guggguggag gaagcugaca caaugaaaa | 720 |
| ucuucaggag auaugcaaag cagaaacccu cgugcaggcc cgaaagagaa agcgaaccag | 780 |
| uaucgagaac cgagugagag caaccugga gaauuguuc cugcagugcc cgaaacccac | 840 |
| acugcagcag aucagccaca ucgcccagca gcuggggcuc gagaaggaug ggccgagu | 900 |
| gugguucugu aaccggcgcc agaagggcaa gcgaucaagc agcgacuaug cacaacgaga | 960 |
| ggauuuugag gcugcggggu cccuuuucuc aggggggacca gugccuuuc ucuggcccc | 1020 |
| agggccccau uuuggguaccc caggcuaugg gagcccucac uucacugcac uguacuccuc | 1080 |
| ggucccuuuc ccugaggggg aagccuuuucc ccugcucucc gucaccacuc ugggcucucc | 1140 |
| caugcauuca aacugaggug ccugcccuuc uaggaauggg ggacaggggg aggggaggag | 1200 |
| cuagggaaag aaaaccugga guuguugcca gggguuuugg gauuaaguuc uucauucacu | 1260 |

```
aaggaaggaa uugggaacac aaagggaggg ggcagggag uuuggggcaa cugguuggag    1320
ggaaggugaa guucaaugau gcucuugauu uuaaucccac aucauguauc acuuuuuucu    1380
uaaauaaaga agccugggac acaguagaua gacacacuua aaaaaaaaaa               1430

<210> SEQ ID NO 5
<211> LENGTH: 57
<212> TYPE: RNA
<213> ORGANISM: Artificial Sequence
<220> FEATURE:
<223> OTHER INFORMATION: shRNA#1 of CSNK2A1

<400> SEQUENCE: 5
ccggccgagu ugcuucucga uauuucucga gaaauaucga gaagcaacuc gguuuug       57

<210> SEQ ID NO 6
<211> LENGTH: 58
<212> TYPE: RNA
<213> ORGANISM: Artificial Sequence
<220> FEATURE:
<223> OTHER INFORMATION: shRNA#2 of CSNK2A1

<400> SEQUENCE: 6
ccggacagac uaugacauuc gauuucucga gaaaucgaau gucauagucu guuuuuug      58

<210> SEQ ID NO 7
<211> LENGTH: 14
<212> TYPE: PRT
<213> ORGANISM: Artificial Sequence
<220> FEATURE:
<223> OTHER INFORMATION: epitope of OCT4

<400> SEQUENCE: 7

Ser Val Pro Val Thr Ala Leu Gly Ser Pro Met His Ser Asn
1               5                   10

<210> SEQ ID NO 8
<211> LENGTH: 14
<212> TYPE: PRT
<213> ORGANISM: Artificial Sequence
<220> FEATURE:
<223> OTHER INFORMATION: epitope of OCT4

<400> SEQUENCE: 8

Pro Ser Val Pro Val Thr Ala Leu Gly Ser Pro Met His Ser
1               5                   10
```